(12) United States Patent
Warner

(10) Patent No.: US 10,208,070 B2
(45) Date of Patent: *Feb. 19, 2019

(54) SYNTHETIC BLEND F-POSS COMPOSITIONS FORMED FROM MULTIPLE FEEDSTOCK MATERIALS

(71) Applicant: NBD NANOTECHNOLOGIES, INC., Danvers, MA (US)

(72) Inventor: John Charles Warner, Wilmington, MA (US)

(73) Assignee: NBD NANOTECHNOLOGIES, INC., Danvers, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/230,697

(22) Filed: Aug. 8, 2016

(65) Prior Publication Data

US 2017/0183364 A1 Jun. 29, 2017

Related U.S. Application Data

(63) Continuation of application No. 14/876,911, filed on Oct. 7, 2015, now Pat. No. 9,409,933.

(60) Provisional application No. 62/060,622, filed on Oct. 7, 2014.

(51) Int. Cl.

| | |
|---|---|
| *C08G 77/24* | (2006.01) |
| *C07F 7/21* | (2006.01) |
| *C08K 5/549* | (2006.01) |
| *C08L 83/04* | (2006.01) |
| *C09D 183/08* | (2006.01) |
| *C08G 77/04* | (2006.01) |

(52) U.S. Cl.
CPC .............. *C07F 7/21* (2013.01); *C08G 77/045* (2013.01); *C08G 77/24* (2013.01); *C08K 5/549* (2013.01); *C08L 83/04* (2013.01); *C09D 183/08* (2013.01)

(58) Field of Classification Search
CPC .............................. C08G 77/24; C08G 77/045
See application file for complete search history.

(56) References Cited

U.S. PATENT DOCUMENTS

| | | |
|---|---|---|
| 6,716,919 B2 | 4/2004 | Lichtenhan et al. |
| 7,193,015 B1 | 3/2007 | Mabry et al. |
| 2008/0221262 A1 | 9/2008 | Mabry et al. |
| 2010/0035070 A1 | 2/2010 | Moorlag et al. |
| 2010/0222503 A1 | 9/2010 | Laine et al. |
| 2013/0072609 A1 | 3/2013 | Haddad et al. |
| 2014/0238263 A1 | 8/2014 | Scheonfisch et al. |
| 2014/0323005 A1 | 10/2014 | Dooley et al. |

FOREIGN PATENT DOCUMENTS

| | | |
|---|---|---|
| CN | 1100838 C | 2/2003 |
| CN | 101875707 A | 11/2010 |
| EP | 2248849 A1 | 11/2010 |

OTHER PUBLICATIONS

Mabry et al.; Fluorinated Polyhedral Oligomeric Silsesquioxanes (F-POSS); Angew. Chem. Int. Ed.; May 19, 2008; vol. 47, Issue 22; pp. 4137-4140.
Mabry; Nanostructured Materials; In-House Report; Air Force Research Laboratory; Aug. 2012; pp. 1-63.
International Preliminary Report on Patentability for International Patent Application No. PCT/US2015/054367; dated Apr. 20, 2017.
Search Report for European Patent Application No. 15849377.5; dated May 17, 2018.
Mabry; Nanostructured Materials; Air Force Research Laboratory (AFMC); Aug. 2012.

*Primary Examiner* — Margaret G Moore
(74) *Attorney, Agent, or Firm* — Barnes & Thornburg LLP; Jason Bernstein

(57) ABSTRACT

The present disclosure relates, in exemplary embodiments, to compositions of matter comprising synthetic blends of at least two feedstocks that produce a distribution of fluorinated polyhedral oligomeric silsesquioxane molecule structures. The present disclosure also relates, in exemplary embodiments, to methods of making such synthetic blends.

20 Claims, 16 Drawing Sheets

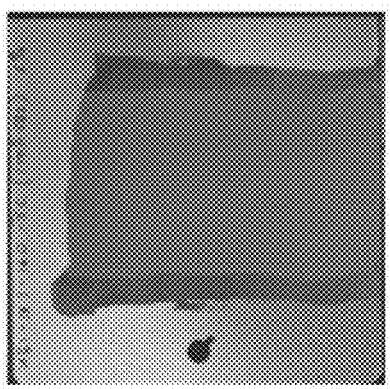
Fig. 13A
Fig. 13B
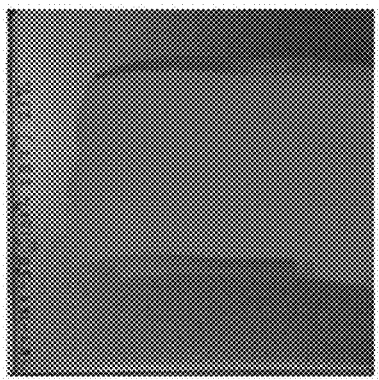
Fig. 13C
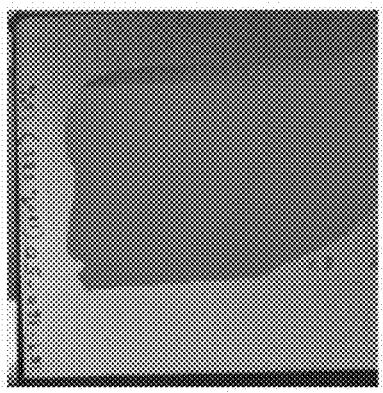
Fig. 13D

SYNTHETIC BLEND F-POSS COMPOSITIONS FORMED FROM MULTIPLE FEEDSTOCK MATERIALS

CROSS REFERENCE TO RELATED APPLICATION

This application is a continuation of U.S. patent application Ser. No. 14/876,911, filed Oct. 7, 2015, which issued as U.S. Pat. No. 9,409,933 on Aug. 9, 2016, which claims the benefit of U.S. Provisional Patent Application No. 62/060,622, filed Oct. 7, 2014, the contents of which are incorporated herein by reference in their entireties.

FIELD

The present disclosure relates, in exemplary embodiments, to compositions of matter comprising synthetic blends of at least two feedstocks that produce a distribution of fluorinated polyhedral oligomeric silsesquioxane molecule structures. The present disclosure also relates, in exemplary embodiments, to methods of making such synthetic blends.

BACKGROUND

Fluorinated polyhedral oligomeric silsesquioxane ("F-POSS") molecules are a subclass of polyhedral oligomeric silsesquioxanes ("POSS") which consists of a silicon-oxide core [$SiO_{1.5}$] with a periphery of long-chain fluorinated alkyl groups. Such alkyl groups include fluorinated triethoxysilanes. F-POSS molecules possess some of the lowest known surface energies leading to the creation of superhydrophobic and oleophobic surfaces. A feature of F-POSS material is that it ordinarily forms a siloxy cage that acts like an inorganic glass-like material, but have organic R group substituents at the matrix apices, which provides unusual properties and applications. See formula [1] below. Each R substituent can be labeled as, for example, R1, R2, R3, R4, R5, R6, R7 or R8. See formula [2] below.

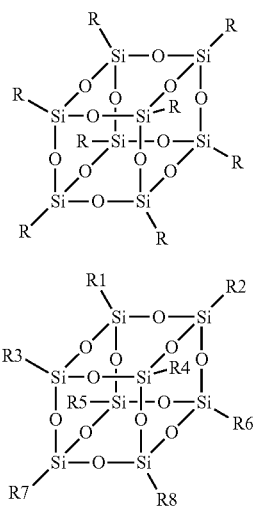

[1]

[2]

It is believed that heretofore F-POSS materials have been formed having only one molecule as the R substituent for all apices. See for example, the following U.S. patents and published applications: U.S. Pat. No. 6,716,919 (issued to Lichtenhan et al.), U.S. Pat. No. 7,195,015 (issued to Mabry et al.), 2008/0221262 (filed by Mabry et al.), and 2013/0072609 (filed by Haddad et al.). The fluorine atoms of neighboring F-POSS molecules have a tendency to attract each other resulting in F-POSS molecules not typically being readily dispersible or dissociable in other materials. F-POSS molecules typically have low solubility in non-fluorinated solvents. It would be desirable to have an F-POSS material that was more easily dispersed or dissociated in other materials.

SUMMARY

In one aspect, the disclosure provides an F-POSS compound of the formula

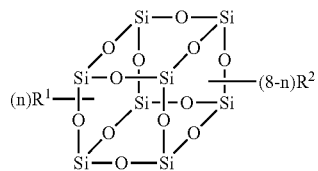

or a mixture thereof, wherein $R^1$ and $R^2$ are each independently long-chain fluorinated alkyl, and n is an integer from 0 to 8, provided that $R^1$ and $R^2$ are different.

In another aspect, the disclosure provides an F-POSS composition comprising a mixture of compounds of the formula

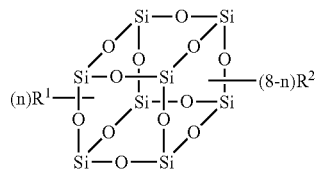

wherein $R^1$ and $R^2$ are each independently long-chain fluorinated alkyl, and n is an integer from 0 to 8, provided that $R^1$ and $R^2$ are different.

In another aspect, the disclosure provides an F-POSS composition produced by a process comprising:
contacting a first feedstock comprising a first fluorinated trialkoxysilane with a second feedstock comprising a second fluorinated trialkoxysilane, wherein the first fluorinated trialkoxysilane and the second fluorinated trialkoxysilane are different.

In another aspect, the disclosure provides a polymer synthetic blend composition of fluorinated polyhedral oligomeric silsesquioxane ("F-POSS") comprising, a mixture of feedstock materials comprising
a. a first feedstock comprising a first fluorinated triethoxysilane having a carbon chain length of $C_1x$, where x is the number of carbons; and,
b. a second feedstock comprising a second fluorinated triethoxysilane having a carbon chain length of $C_2y$, where y is the number of carbons, wherein x is greater than y,
wherein the polymer blend composition resulting from the mixing of the first and second feedstocks comprises a distribution of molecules, each molecule comprising a matrix structure having eight apices, each apex having a substituent R, each substituent R having a carbon chain length Cn, such that a portion of the distribution of molecules has all substituents R having the same carbon chain length Cn and a portion of the distribution of molecules has at least one substituent R1 having a carbon chain length $C_1x$ and R2 having a carbon chain length $C_2y$ wherein C1 is greater than C2.

In another aspect, the disclosure provides a polymer synthetic blend composition of fluorinated polyhedral oligomeric silsesquioxane ("F-POSS") comprising, a mixture of feedstock materials comprising
  a. a first feedstock comprising a first fluorinated triethoxysilane having a carbon chain length of $C_1x$, where x is a number of carbon atoms; and,
  b. a second feedstock comprising a second fluorinated triethoxysilane having a carbon chain length of $C_2y$, where y is a number of carbon atoms, wherein x is not equal to y,
  wherein the polymer blend composition resulting from the mixing of the first and second feedstocks comprises a distribution of molecules, each molecule comprising a matrix structure having eight apices, each apex having a substituent R, each substituent R having a carbon chain length Cn, such that a portion of the distribution of molecules has all substituents R having the same carbon chain length Cn and a portion of the distribution of molecules has at least one substituent R1 having a carbon chain length $C_1x$ and R2 having a carbon chain length $C_2y$ wherein C1 is greater than C2.

In another aspect, the disclosure provides a polymer synthetic blend composition, comprising: polymerized units of a first feedstock comprising a second fluorinated triethoxysilane having a carbon chain length of $C_1x$, where x is the number of carbons, and x is a range of 4-10; and a second feedstock comprising a second fluorinated triethoxysilane having a carbon chain length of $C_2y$, where y is the number of carbons, and y is a range of 4-10, wherein x is greater than y.

In another aspect, the disclosure provides a method of forming an F-POSS polymer synthetic blend material having a distribution of apex substituents, comprising:
  a. providing a first feedstock comprising a first fluorinated triethoxysilane having a carbon chain length of $C_1x$, where x is the number of carbons, and x is a range of 4-10;
  b. providing a second feedstock comprising a second fluorinated triethoxysilane having a carbon chain length of $C_2y$, where y is the number of carbons, and y is a range of 4-10, wherein x is greater than y; and
  c. reacting the first feedstock with the second feedstock under conditions so as to form a distribution of molecules, each molecule comprising a matrix structure having eight apices, each apex having a substituent R, each substituent R having a carbon chain length Cn in which n is in a range of 4-10, such that a portion of the distribution of molecules has all substituents R having the same carbon chain length Cn and a portion of the distribution of molecules has at least one substituent R1 having a carbon chain length $C_1x$ and R2 having a carbon chain length $C_2y$ wherein C1 is greater than C2.

In another aspect, the disclosure provides a paint composition, comprising:
  a. at least one polymer base paint material; and
  b. a polymer synthetic blend composition comprising polymer synthetic blend composition of fluorinated polyhedral oligomeric silsesquioxane ("F-POSS"), comprising: a mixture of feedstock materials comprising
    i. a first feedstock comprising a first fluorinated triethoxysilane having a carbon chain length of $C_1x$, where x is the number of carbons, and,
    ii. a second feedstock comprising a second fluorinated triethoxysilane having a carbon chain length of $C_2y$, where y is the number of carbons, wherein x is greater than y,
  whereby the polymer blend composition resulting from the mixing of the first and second feedstocks comprises a distribution of molecules, each molecule comprising a matrix structure having eight apices, each apex having a substituent R, each substituent R having a carbon chain length Cn, such that a portion of the distribution of molecules has all substituents R having the same carbon chain length Cn and a portion of the distribution of molecules has at least one substituent R1 having a carbon chain length $C_1x$ and R2 having a carbon chain length $C_2y$ wherein C1 is greater than C2.

The compounds of the present disclosure can be described as embodiments in any of the following enumerated clauses. It will be understood that any of the embodiments described herein can be used in connection with any other embodiments described herein to the extent that the embodiments do not contradict one another.

1. A polymer synthetic blend composition of fluorinated polyhedral oligomeric silsesquioxane ("F-POSS"), comprising: a mixture of feedstock materials comprising
  a. a first feedstock comprising a first fluorinated triethoxysilane having a carbon chain length of $C_1x$, where x is the number of carbons; and,
  b. a second feedstock comprising a second fluorinated triethoxysilane having a carbon chain length of $C_2y$, where y is the number of carbons, wherein x is greater than y,
  whereby the polymer blend composition resulting from the mixing of the first and second feedstocks comprises a distribution of molecules, each molecule comprising a matrix structure having eight apices, each apex having a substituent R, each substituent R having a carbon chain length Cn, such that a portion of the distribution of molecules has all substituents R having the same carbon chain length Cn and a portion of the distribution of molecules has at least one substituent R1 having a carbon chain length $C_1x$ and R2 having a carbon chain length $C_1y$ wherein C1 is greater than C2.

2. The polymer synthetic blend composition of clause 1, wherein the first feedstock is 1H, 1H, 2H, 2H nonafluorohexyltriethoxysilane.

3. The polymer synthetic blend composition of clause 1 or 2, wherein the second feedstock is 1H, 1H, 2H, 2H perfluorooctyltriethoxysilane.

4. The polymer synthetic blend composition of any one of clauses 1 to 3, wherein the first feedstock and the second feedstock are present in a molar ratio in a range of from 1:3 to 3:1.

5. The polymer synthetic blend composition of any one of clauses 1 to 4, wherein the melting temperature of the polymer blend composition is at least about 30 degrees lower than the melting temperature of either the first feedstock or the second feedstock alone.

6. The polymer synthetic blend composition of any one of clauses 1 to 5, wherein x is in a range of 1-16 and y is in a range of 1-16.

7. The polymer synthetic blend composition of any one of clauses 1 to 6, wherein x is in a range of 4-10 and y is in a range of 4-10.

A polymer synthetic blend composition, comprising: a mixture of at least two feedstock materials comprising
  a. a first feedstock comprising a first fluorinated triethoxysilane having a carbon chain length of $C_1x$, where x is the number of carbons;

b. a second feedstock comprising a second fluorinated triethoxysilane having a carbon chain length of $C_2y$, where y is the number of carbons, wherein x is not equal to y, and whereby the polymer blend composition resulting from the mixing of the at least two feedstocks comprises a distribution of molecules, each molecule comprising a matrix structure having eight apices, each apex having a substituent R, each substituent R having a carbon chain length Cn, such that a portion of the distribution of molecules has all substituents R having the same carbon chain length Cn and a portion of the distribution of molecules has at least one substituent R1 having a carbon chain length $C_1x$ and R2 having a carbon chain length $C_2y$ wherein C1 is greater than C2.

8. The polymer synthetic blend composition of clause 7, wherein x is in a range of 1-16 and y is in a range of 1-16.

9. The polymer synthetic blend composition of clause 7 or 8, wherein x is in a range of 4-10 and y is in a range of 4-10.

10. A polymer synthetic blend composition, comprising: polymerized units of a first feedstock comprising a second fluorinated triethoxysilane having a carbon chain length of $C_1x$, where x is the number of carbons, and x is a range of 4-10; and a second feedstock comprising a second fluorinated triethoxysilane having a carbon chain length of $C_1y$, where y is the number of carbons, and y is a range of 4-10, wherein x is greater than y.

11. A method of forming an F-POSS polymer synthetic blend material having a distribution of apex substituents, comprising:

a. providing a first feedstock comprising a first fluorinated triethoxysilane having a carbon chain length of $C_1x$, where x is the number of carbons, and x is a range of 4-10;

b. providing a second feedstock comprising a second fluorinated triethoxysilane having a carbon chain length of $C_1y$, where y is the number of carbons, and y is a range of 4-10, wherein x is greater than y; and c. reacting the first feedstock with the second feedstock under conditions so as to form a distribution of molecules, each molecule comprising a matrix structure having eight apices, each apex having a substituent R, each substituent R having a carbon chain length Cn in which n is in a range of 4-10, such that a portion of the distribution of molecules has all substituents R having the same carbon chain length Cn and a portion of the distribution of molecules has at least one substituent R1 having a carbon chain length $C_1x$ and R2 having a carbon chain length C1y wherein C1 is greater than C2.

12. A polymer synthetic blend composition of fluorinated polyhedral oligomeric silsesquioxane ("F-POSS"), comprising: a mixture of feedstock materials comprising a. a first feedstock comprising a first fluorinated triethoxysilane having a carbon chain length of $C_1x$, where x is the number of carbons; and b. a second feedstock comprising a second fluorinated triethoxysilane having a carbon chain length of $C_2y$, where y is the number of carbons, wherein x is greater than y, whereby the polymer blend composition resulting from the mixing of the first and second feedstocks comprises a distribution of molecules, each molecule comprising a matrix structure having eight apices, each apex having a substituent R, each substituent R having a carbon chain length Cn in which n is in a range of 4-10, such that a portion of the distribution of molecules has all substituents R having the same carbon chain length Cn and a portion of the distribution of molecules has at least one substituent R1 having a carbon chain length $C_1x$ and R2 having a carbon chain length $C_2y$ wherein C1 is greater than C2.

13. A polymer synthetic blend composition of fluorinated polyhedral oligomeric silsesquioxane ("F-POSS"), comprising: a mixture of feedstock materials comprising a. a first feedstock comprising a first fluorinated triethoxysilane having a carbon chain length of $C_1x$, where x is the number of carbons; and b. a second feedstock comprising a second fluorinated triethoxysilane having a carbon chain length of $C_2y$, where y is the number of carbons, wherein x is greater than y, whereby the polymer blend composition resulting from the mixing of the first and second feedstocks comprises a distribution of molecules, each molecule comprising a matrix structure having eight apices, each apex having a substituent R, each substituent R having a carbon chain length Cn in which n is in a range of 4-10, such that a first portion of the distribution of molecules formed have substituent R having a C1x:C2y ratio of 1:0, a second portion of the distribution of molecules formed have substituent R having a C1x:C2y ratio of 0:1, and a third portion of the molecules have substituent R having a C1x:C2y ratio in a range of from 1:7 to 7:1.

14. A paint composition, comprising:

a. at least one polymer base paint material; and b. a polymer synthetic blend composition comprising polymer synthetic blend composition of fluorinated polyhedral oligomeric silsesquioxane ("F-POSS"), comprising: a mixture of feedstock materials comprising i. a first feedstock comprising a first fluorinated triethoxysilane having a carbon chain length of $C_1x$, where x is the number of carbons, and, ii. a second feedstock comprising a second fluorinated triethoxysilane having a carbon chain length of $C_1y$, where y is the number of carbons, wherein x is greater than y, whereby the polymer blend composition resulting from the mixing of the first and second feedstocks comprises a distribution of molecules, each molecule comprising a matrix structure having eight apices, each apex having a substituent R, each substituent R having a carbon chain length Cn, such that a portion of the distribution of molecules has all substituents R having the same carbon chain length Cn and a portion of the distribution of molecules has at least one substituent R1 having a carbon chain length $C_1x$ and R2 having a carbon chain length $C_2y$ wherein C1 is greater than C2

15. The paint composition of clause 14, wherein the polymer base paint material comprises at least one material selected from the group consisting of a polyurethane, polyester, polypropylene, polybutylene, poly(L-lactic acid), polycellulosic, polyhydroxy alkanate, lignose cellulose, polyethylene oxide, epoxy, epoxy resin, alkyd resin, polyether, and mixtures of at least two of the foregoing.

16. The paint composition of clause 14 or 15, wherein the paint composition has a water contact angle of at least 110 degrees and a hexadecane contact angle of at least 70 degrees.

17. The paint composition of any one of clauses 14 to 16, wherein the polymer synthetic blend composition has a solubility in the at least one polymer base paint material of 70% solids comprised of polyurethanes diluted in at least one material selected from the group consisting of toluene, methyl ethyl ketone, IPA and xylene.

18. A method of forming an F-POSS polymer synthetic blend material having a distribution of apex substituents, comprising:

a. providing a first feedstock comprising a first fluorinated triethoxysilane having a carbon chain length of $C_1x$, where x is the number of carbons, and x is a range of 4-10;

b. providing a second feedstock comprising a second fluorinated triethoxysilane having a carbon chain length of $C_1y$, where y is the number of carbons, and y is a range of 4-10, wherein x is greater than y; and c. reacting the first feedstock with the second feedstock under conditions so as to form a distribution of molecules, each molecule comprising a matrix structure having eight apices, each apex having a substituent R, each substituent R having a carbon chain length in which n is in a range of 4-10, such that a portion of the distribution of molecules has all substituents R having the same carbon chain length Cn and a portion of the distribution of molecules has at least one substituent R1 having a carbon chain length $C_1x$ and R2 having a carbon chain length $C_1y$ wherein C1 is greater than C2.

19. An F-POSS compound of the formula

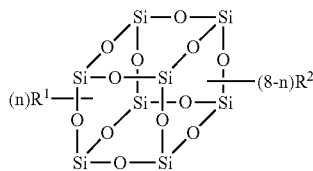

or a mixture thereof, wherein $R^1$ and $R^2$ are each independently long-chain fluorinated alkyl, and n is an integer from 0 to 8, provided that $R^1$ and $R^2$ are different.

20. The F-TOSS compound of clause 19, wherein each long-chain fluorinated alkyl is independently from 5 to 12 carbon atoms in the longest continuous chain of carbon atoms.

21. The F-POSS compound of clause 19 or 20, wherein each long-chain fluorinated alkyl is independently selected from the group consisting of 4/2 fluorinated alkyl, 3/3 fluorinated alkyl, 6/2 fluorinated alkyl, 4/4 fluorinated alkyl, 8/2 fluorinated alkyl and 6/4 fluorinated alkyl.

22. The F-POSS compound of any one of clauses 19 to 21, wherein $R^1$ is 4/2 fluorinated alkyl and $R^2$ is 6/2 fluorinated alkyl.

23. An F-POSS composition comprising a mixture of compounds of the formula

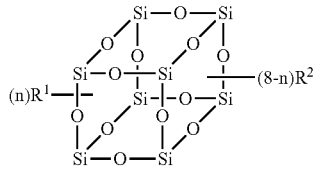

wherein $R^1$ and $R^2$ are each independently long-chain fluorinated alkyl, and n is an integer from 0 to 8, provided that $R^1$ and $R^2$ are different.

24. The F-POSS composition of clause 23, wherein each long-chain fluorinated alkyl is independently from 5 to 12 carbon atoms in the longest continuous chain of carbon atoms.

25. The F-POSS composition of clause 23 or 24, wherein each long-chain fluorinated alkyl is independently selected from the group consisting of 4/2 fluorinated alkyl, 3/3 fluorinated alkyl, 6/2 fluorinated alkyl, 4/4 fluorinated alkyl, 8/2 fluorinated alkyl and 6/4 fluorinated alkyl.

26. The F-POSS composition of any one of clauses 23 to 25, wherein $R^1$ is 4/2 fluorinated alkyl and $R^2$ is 6/2 fluorinated alkyl.

27. The F-POSS composition of any one of clauses 23 to 26, wherein the mixture of compounds comprises a distribution of compounds having a ratio of $R^1$ to $R^2$ between 0:8 to 8:0.

28. The F-POSS composition of clause 27, wherein the distribution is a Gaussian distribution.

29. An F-POSS composition produced by a process comprising:

contacting a first feedstock comprising a first fluorinated trialkoxysilane with a second feedstock comprising a second fluorinated trialkoxysilane, wherein the first fluorinated trialkoxysilane and the second fluorinated trialkoxysilane are different.

30. The F-POSS composition of clause 29, wherein the first fluorinated trialkoxysilane is of the formula $R^1Si(OR^A)_3$, and the second fluorinated trialkoxysilane is of the formula $R^2Si(OR^B)_3$, wherein each of $R^1$ and $R^2$ are independently a long-chain fluorinated alkyl, each $R^A$ and $R^B$ is independently $C_1$-$C_6$ alkyl, provided that $R^1$ and $R^2$ are different.

31. The F-POSS composition of clause 30, wherein each long-chain fluorinated alkyl is independently from 5 to 12 carbon atoms in the longest continuous chain of carbon atoms.

32. The F-POSS composition of clause 30, wherein each long-chain fluorinated alkyl is independently selected from the group consisting of 4/2 fluorinated alkyl, 3/3 fluorinated alkyl, 6/2 fluorinated alkyl, 4/4 fluorinated alkyl, 8/2 fluorinated alkyl and 6/4 fluorinated alkyl.

33. The F-POSS composition of any one of clauses 29 to 32, wherein $R^1$ is 4/7 fluorinated alkyl and $R^2$ is 6/2 fluorinated alkyl.

34. The F-POSS composition of any one of clauses 29 to 33, wherein the composition comprises a mixture of compounds in a distribution having a ratio of $R^1$ to $R^2$ between 0:8 to 8:0.

35. The F-TOSS composition of clause 34, wherein the distribution is a Gaussian distribution.

BRIEF DESCRIPTION OF THE DRAWINGS

The drawings disclose exemplary embodiments in which like reference characters designate the same or similar parts throughout the figures of which:

FIG. 13A is a photograph of coated steel containing SB3 at 1 wt %.

FIG. 13B is a photograph of coated steel containing SB3 at 5 wt %.

FIG. 13C is a photograph of coated steel containing SB3 at 10 wt %.

FIG. 13D is a photograph of coated steel containing SB3 at 25 wt %.

DETAILED DESCRIPTION

Figure 1:
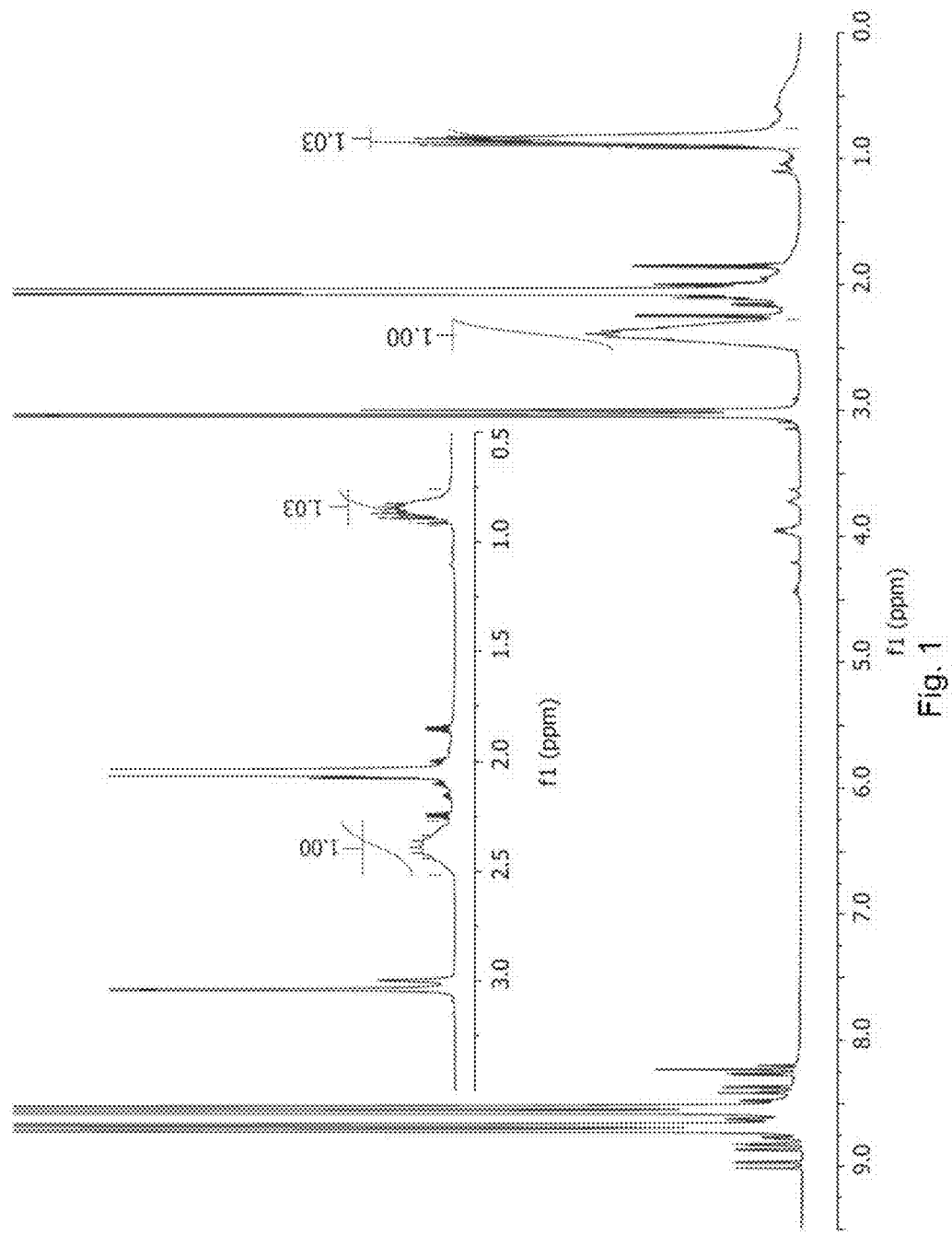
FIG. 1 is an analysis plot of $^1H$ NMR analysis for a synthetic blend SB1 according to Example 1A(i).

Silsesquioxanes have a cage-like structure, which is most commonly a cube, hexagonal prism, octagonal prism, decagonal prism, or dodecagonal prism. In exemplary embodiments, of the various possible F-POSS cage molecular structures, the cube-like ("T8") cage structure is formed. In exemplary embodiments, the present disclosure provides F-TOSS compositions made of a blend of feedstock materials. In one exemplary embodiment, a first feedstock comprises a first fluorinated triethoxysilane and a second feedstock comprises a second fluorinated triethoxysilane. Each fluorinated triethoxysilane has a distinct carbon chain length C. In exemplary embodiments, C is in a range of 4-10. In exemplary embodiments, C is in a range of 4-10. In exemplary embodiments, C is 4, 6, 8 or 10. In exemplary embodiments, a first feedstock may be a C6 fluoroalkyl molecule and the second feedstock may be a C8 fluoroalkyl molecule. In exemplary embodiments, a first feedstock may be 1H, 1H, 2H, 2H nonafluorohexyltriethoxysilane. In exemplary embodiments, a second feedstock may be 1H, 1H, 2H, 2H perfluorooctyltriethoxysilane (a.k.a. 1H, 1H, 2H, 2H decatriafluorooctyltriethoxysilane)

As used herein, the term "long-chain fluorinated alkyl" means any straight chain or branched chain alkyl group having from 5 to 12 carbon atoms in the longest continuous chain of carbon atoms as counted from the point of attachment of the chain of carbon atoms to the silicon atom at any apex of the silicon-oxide core, where at least one hydrogen atom in the straight chain or branched chain alkyl group is replaced by a fluorine atom. Any number of hydrogen atoms in the straight chain or branched chain alkyl group can be replaced with fluorine atoms within the meaning of "long-chain fluorinated alkyl" as used herein. For example, the terminal methyl group of a straight chain alkyl group having six carbon atoms in the chain (e.g. a hexyl group) can have each of the pendent hydrogen atoms replaced by a fluorine atom (e.g. a trifluoromethyl) to provide a long chain fluorinated alkyl group having the formula —CH$_2$CH$_2$CH$_2$CH$_2$CH$_2$CF$_3$. In another example, the last two carbon atoms of a straight chain alkyl group having six carbon atoms in the chain can have each of the pendent hydrogen atoms replaced by a fluorine atom (e.g. a trifluoroethyl) to provide a long chain fluorinated alkyl group having the formula —CH$_2$CH$_2$CH$_2$CH$_2$CF$_2$CF$_3$. This exemplary pattern can be continued to include within the definition of "long chain fluorinated alkyl" groups of the formula —CH$_2$CH$_2$CH$_2$CF$_2$CF$_2$CF$_3$, —CH$_2$CH$_2$CF$_2$CF$_2$CF$_2$CF$_3$, —CH$_2$CF$_2$CF$_2$CF$_2$CF$_2$CF$_3$, and —CF$_2$CF$_2$CF$_2$CF$_2$CF$_2$CF$_3$. As is commonly known in the art, an alkyl group where every hydrogen atoms in the chain is replaced by a fluorine atom is known as a "perfluorinated" alkyl group. In some embodiments, the term perfluorinated is used in connection with a group where some carbon atoms are defined to have hydrogen atoms bonded thereto, while other carbon atoms have all fluorine atoms bonded thereto. For example, the nomenclature 1H, 1H, 2H, 2H perfluorooctyltriethoxysilane describes a compound in which the two terminal carbon atoms at the point of covalent attachment of the chain to the F-POSS have hydrogen atoms bound to the carbon atom, while the remainder of the carbon atoms in the chain have fluorine atoms bonded thereto and are thus are perfluorinated.

When less than all of the carbon atoms in the longest continuous chain of carbon atoms have hydrogens replaced by fluorine atoms, the "long chain fluorinated alkyl" group can be identified by the shorthand X/Y, where X is the number of terminal carbon atoms in the longest continuous chain of carbon atoms as counted from the point of attachment of the chain of carbon atoms to the silicon atom at any apex of the silicon-oxide core, and Y is the remaining number of carbon atoms in the longest continuous chain of carbon atoms on which hydrogen atoms are not replaced by fluorine atoms. For example, a long chain fluorinated alkyl group of the formula —CH$_2$CH$_2$CF$_2$CF$_2$CF$_2$CF$_3$ can be given the shorthand 4/2. Other exemplary long chain fluorinated alkyl groups include but are not limited to 3/3, 6/2, 4/4, 8/2, 6/4 and the like. It will be appreciated that such long chain fluorinated alkyl groups can also be referred to as 4/2 fluorinated alkyl, 3/3 fluorinated alkyl, 6/2 fluorinated alkyl, 4/4 fluorinated alkyl, 8/2 fluorinated alkyl, 6/4 fluorinated alkyl, and the like When the shorthand X/Y is used herein in connection with F-POSS, the name provided refers to the F-POSS molecule each of the groups attached to the apices of the silicon-oxide core is of the long chain fluorinated alkyl group type defined by the X/Y. For example, 6/2 F-POSS refers to an F-POSS molecule of Formula [1], wherein each of the R groups at the apices of the silicon-oxide core is a 6/2 long chain fluorinated alkyl group as defined herein.

As examples, formulae for 6/2 F-POSS [3] and 4/2 F-POSS [4] molecules are shown below.

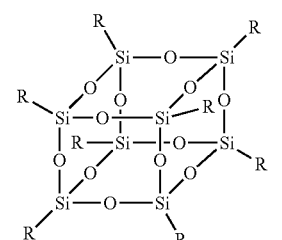

6/2 F-POSS
R = CH$_2$CH$_2$CF$_2$CF$_2$CF$_2$CF$_2$CF$_2$CF$_3$

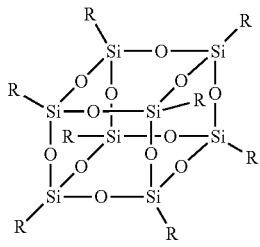

4/2 F-POSS
R = CH$_2$CH$_2$CF$_2$CF$_2$CF$_2$CF$_3$

In conventional F-POSS synthesis, the F-POSS molecule has a matrix structure having eight apices, each apex comprising silicon. Each apex has a substituent moiety R, which comprises a C—F chain having a carbon chain length Cn, where n is the number of carbons in the chain. 6/2 F-POSS is a C8 molecule as the R substituent has 8 carbons. This F-POSS is designated as 6/2 as it has 6 C—F groups and 2 C—H groups. 4/2 F-POSS is a C6 molecule as the R substituent has 6 carbons comprising 4 C—F groups and 2 C—H groups.

In exemplary embodiments of the present compositions, a blend of several distinct F-POSS molecules is synthesized from a first feedstock fluorinated triethoxysilane and a second feedstock fluorinated triethoxysilane, each feedstock being a different fluorinated triethoxysilane. The end product synthesized is a distribution of F-POSS molecules having portions made up of distinct F-POSS molecules with one of several R substituents (e.g., R$^1$, R$^2$, R$^3$, etc.). A portion of the F-POSS molecules have a matrix structure having all eight apices with a substituent R$^1$ and having the same carbon chain length C. A portion of the molecules will have all eight apices with a substituent R$^2$. Formula [5] below shows a molecular formula with (n)R$^1$ units and (8-n)R$^2$ units, where n is the number of units, and each R$^1$ and/or R$^2$ unit is covalently attached to a silicon atom apex of the cube-like structure. It will be appreciated that n in the formula [5] is an integer from 0 to 8.

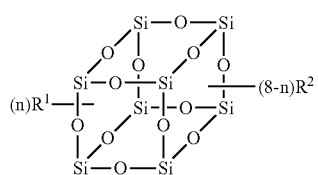

[5]

A portion of the molecules have a matrix structure in which one or more apices have a substituent R$^1$ and the remainder have a substituent R$^2$, where R$^1$ and R$^2$ have different carbon chain lengths (e.g. C1 and C2). In the present compositions, the blend of molecules may, in exemplary embodiments, form a Gaussian distribution of molecules having different ratios of R$^1$ and R$^2$. For example, in one exemplary embodiment, one portion of the blend may be made up of an F-POSS molecule with a molar ratio of R$^1$:R$^2$=0:8, in other words, all eight apices have R$^2$. Another portion may have a molar ratio of R$^1$:R$^2$=1:7, in other words, seven of the apices have R$^2$ and one apex has R$^1$. Another portion has a ratio of 2:6. And, other portions have ratios of 3:5, 4:4, 5:3, 6:2, 7:1 and 8:0. In exemplary embodiments, the distribution of R$^1$:R$^2$ ratios generally comprises a Gaussian distribution. In exemplary embodiments, the distribution of ratios can be predetermined to an extent, or tuned, based on reaction conditions and amounts used of each substituent.

In one exemplary embodiment, a synthetic blend F-POSS was formed of 50% C4 and 50% C6 chain length R substituent molecules.

In some embodiments, the processes described herein can be represented by the following general scheme:

[5]

R$^1$Si(OR$^A$)$_3$ + R$^2$Si(OR$^B$)$_3$ ⟶

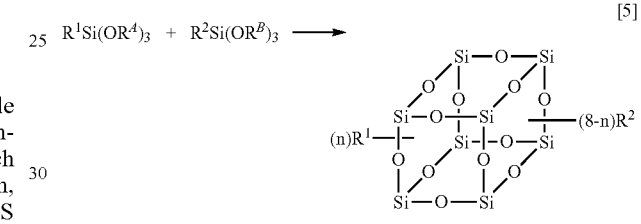

wherein R$^1$ and R$^2$ are as defined above, n is an integer from 0 to 8, and each R$^A$ and R$^B$ is independently an C$_1$-C$_6$ alkyl group, such as methyl, ethyl, n-propyl, iso-propyl, n-butyl, sec-butyl, iso-butyl, n-pentyl, sec-pentyl, and the like. In some embodiments, each R$^A$ and R$^B$ is ethyl.

In exemplary embodiments, three or more feedstocks can be used, each feedstock comprising fluoroalkyl molecule having a different carbon chain length, i.e., a first feedstock may be a fluoroalkyl molecule having a carbon chain length C4, the second feedstock may have the carbon chain length C6, and the third feedstock may have the carbon chain length C8. The distribution of F-POSS molecules formed therefrom will have some F-POSS molecules having the C4 substituent at all eight apices; other molecules in the distribution will have all eight apices having the C6 substituent at all eight apices; still other molecules will have all eight apices having the C8 substituent; and, still other molecules in the distribution blend will have one apex with C4, a second apex with C6, and a third apex with C8, the other apices each having a C4, C6, or C8 substituent; with various other molecules in the distribution blend having different ratios of C4, C6 and C8 at the apices. Exemplary ratios in a blend of F-POSS molecules prepared from three feedstocks of chain length C4, C6 and C8 include, but are not limited to, 0:0:8, 0:1:7, 1:0:7, 1:1:6, 0:2:6, 2:0:6, 1:2:5, 2:1:5, 0:3:5, 3:0:5, 0:4:4, 4:0:4, 1:3:4, 3:1:4, 2:2:4, 0:4:4, 4:0:4, 2:4:2, 4:2:2, 1:4:3, 3:4:1, 5:0:3, 5:3:0, 5:1:2, 5:2:1, 6:0:2, 6:2:0, 6:1:1, 7:0:1, 7:1:0, 0:8:0, 8:0:0, and the like. It will be appreciated that a blend made by the processes described herein can possess any of the ratios above, and any other ratios possible within the distribution provided by the process. It will be further appreciated that it is possible to "tune" the distribution ratio of R substituents based on amounts of feedstocks, reaction conditions and other parameters.

Properties

A feature of exemplary embodiments of the presently disclosed synthetic blend material is that the attraction of F-POSS molecules to each other is reduced due to the variation in different F-POSS molecules in the blend distribution. Some F-POSS molecules synthesized from two different R substituent feedstocks will have all eight apices with the same R substituent, while some molecules will have at least two apices with different R substituents. By making neighboring F-POSS molecules potentially having different R substituents and "look" different to each other, the attractive force of the fluorines of neighboring F-POSS molecules for each other is weakened. This weakened attraction can result in an improved ability of the F-POSS molecules to dissociate or to disperse in other materials.

Formulating a paint material with a fluorinated material has heretofore been difficult because the strong attraction of F-POSS to itself reduces the dissociation in the paint base and often results in aggregation or phase separation, which provides aesthetically unpleasing coating, and also reduces the desirable properties of the paint, such as, but not limited to, surface texture, smoothness, reflectivity, durability, abrasion resistance, and the like. In exemplary embodiments, the synthetic blend of F-POSS molecules can be effectively dispersed in a paint material because the F-POSS molecules are less attracted to each other and will disperse more effectively. This can result in a more even coat and improve physical properties, as well as aesthetic properties. In exemplary embodiments, the synthetic blend F-POSS material of the present disclosure can be formulated into a polymer-based paint. In exemplary embodiments, the paint is a polyurethane-based paint. In exemplary embodiments, the paint is a polyethylene- or polystyrene-based paint. In exemplary embodiments, the paint may contain or be based on at least one of the following: polyester, polypropylene, polybutylene, poly(L-lactic acid), polycellulosic, polyhydroxy alkanate, lignose cellulose, polyethylene oxide, epoxy, epoxy resin, alkyd resin, polyether, and mixtures and combinations of at least two of the foregoing.

In exemplary embodiments, the polymer synthetic blend composition may have a solubility in the polymer base paint material of about 70% solids comprised of polyurethanes diluted in at least one of the following: toluene, methyl ethyl ketone, IPA, xylene and the like.

Another feature of exemplary embodiments of the presently disclosed synthetic blend material is that films and other structures formed therefrom have a degree of "nano-scale roughness" at the molecular level. This nano-scale roughness increases the hydrophobicity of the material, which may provide an increased water contact angle and hydrocarbon contact angle that enhances performance.

With conventional single R substituent F-POSS molecules, conventional wisdom suggests that C4 F-POSS material is less expensive to produce than C6 or C8 F-POSS, without appreciable compromise of performance. Generally speaking, the shorter the carbon chain length, the less repellent the material. However, conventionally, C4 F-POSS may not have the requisite desirable properties to be effective in some applications. In exemplary embodiments, synthetic blend F-POSS materials have been synthesized containing C4 substituents. Such materials have exhibited hexadecane contact angle performance equivalent to C8 F-POSS materials. While not wishing to be bound by any particular theory, such performance enhancement may perhaps be due to the resulting nanostructure of the matrix. See FIGS. 16 and 17 described hereinbelow.

Another feature of exemplary embodiments of the presently disclosed synthetic blend composition when formulated as the SB3 blend, discussed further hereinbelow in the Examples, is that the composition may provide reduced ice adhesion in formulations.

In one aspect of synthetic blend molecules presently disclosed in exemplary embodiments is that the blends demonstrated physical properties not predictable by considering each of the feedstock materials alone. For example, with respect to solubility, discussed in Examples 1B(i-iii), where a 4/2 feedstock and a 6/2 feedstock are used to make the synthetic blend F-POSS composition, the resulting molecular distribution has 0% 6/2 and 100% 4/2 at one side of the graph, and 100% 6/2 and 0% 4/2 at the opposite side of the graph. As the blend ratio of 6/2 and 4/2 changes, a straight line is not achieved. The blend ratio change is not a linear relationship. As the ratio 6/2:4/2 approaches 1:1, solubility increases, but predictably as determined by the endpoints of the blend ratio. Without intending to be bound by any particular theory of the mechanism of action, it may be that the cause of the particular behavior is the activity occurring at a particular level of order in the noncovalent extended matrix.

A unique feature of synthetic blend materials in various exemplary embodiments is that the properties may be customized by adjusting the carbon chain length ratio of the feedstock molecules.

Applications

Exemplary embodiments of compositions disclosed herein may be useful the formulation of protective coatings, such as, but not limited to, repelling oil, water or the like. Exemplary embodiments of compositions disclosed herein may be useful in improving the stability and longevity of formulations containing fluorinated, halogenated or other additive materials that ordinarily would not have adequately stable or durable homogeneity.

In other exemplary embodiments, rather than an F-POSS structure, a non-fluorinated POSS structure may be formed according to methods described herein adapted to replace the fluorine component in at least one of the feedstock materials with another component, or to not use fluorine at all. For example, an alkyl group substituted for the fluorine could make the composition formed more compatible with hydrocarbon systems.

POSS cage structures other than the T8 form may be formed by modifying the methods disclosed herein.

In exemplary embodiments, the feedstock molecules can be chosen based on desired properties to be included in the formed composition. Feedstock molecules may be selected for any of a number of properties or characteristics, including, but not limited to, optimization of compatibilization, inclusion of chromophore or other color-imparting substituent, smell, detectable marker, anti-microbial, or the like. For example, a first feedstock may be one that imparts compatibilization (such as the first feedstock described hereinabove), and a second feedstock may contain a substituent that imparts a color or smell. The resulting F-POSS (or other) molecular distribution will include the characteristics of the feedstock materials.

The following examples are set forth for purposes of illustration only. Parts and percentages appearing in such examples are by weight unless otherwise stipulated.

EXAMPLES

Example 1—6/2:4/2 Fluorinated Polyhedral Oligomeric Silsesquioxane (F-POSS) Synthetic Blends

Example 1A—Synthesis of Materials

Novel proprietary siloxane-caged compounds containing side groups with varying lengths of fluorinated hydrocarbons, essentially a 6/2:4/2 hybrid, were synthesized. For ease of reference, the following nomenclature was used to identify the new synthetic blend (SB) compounds:

SB1: A 3:1 ratio of 1H, 1H, 2H, 2H perfluorooctyltriethoxysilane ("6/2"):1H, 1H, 2H, 2H-Nonafluorohexyltriethoxysilane ("4/2")
SB2: A 1:1 ratio of 1H, 1H, 2H, 2H perfluorooctyltriethoxysilane:1H, 1H, 2H, 2H-Nonafluorohexyltriethoxysilane
SB3: A 1:3 ratio of 1H, 1H, 2H, 2H perfluorooctyltriethoxysilane:1H, 1H, 2H, 2H-Nonafluorohexyltriethoxysilane

Example 1A(i)—SB1 (Ratio of [75% 6/2]:[25% 4/2])

3.83 g of 1H, 1H, 2H, 2H perfluorooctyltriethoxysilane (Sigma Aldrich, 667420-25 g) and 1.03 g of 1H, 1H, 2H, 2H-Nonafluorohexyltriethoxysilane (TCI America, T2860) (3:1 molar ratio) were taken in 10 mL ethanol, to which was added 0.3 mL of KOH solution (7.4 mg/mL). The mixture was stirred at room temperature for 24 hrs resulting in the precipitation of a white semi-solid product. The solvent in the reaction mixture was decanted, the precipitate washed repeatedly with ethanol, then dried under vacuum oven overnight at 45-50° C. The crude product was then dissolved in AK-225G solvent, and then the organic layer washed three times with ddH$_2$O, dried over anhydrous magnesium sulfate, filtered, concentrated and dried under vacuum overnight at 80° C. The resulting purified product was still a semi-solid substance.

Example 1A(ii)—SB2 (Ratio of [50% 6/2]:[50% 4/2])

2.55 g of the 1H, 1H, 2H, 2H perfluorooctyltriethoxysilane (Sigma Aldrich, 667420-25 g) and 2.05 g of 1H, 1H, 2H, 2H-Nonafluorohexyltriethoxysilane (TCI America, T2860) (1:1 molar ratio) were taken in 10 mL ethanol, to which was added 0.3 mL of KOH solution (7.4 mg/mL). The mixture was stirred at room temperature for 24 h resulting in the precipitation of a white semi-solid product. The solvent in the reaction mixture was decanted, the precipitate washed repeatedly with ethanol, then dried under vacuum overnight at 45-50° C. The crude product was then dissolved in AK-225G solvent, and then the organic layer washed three times with ddH$_2$O, dried over anhydrous magnesium sulfate, filtered, concentrated and dried under vacuum overnight at 80° C. The resulting purified product was still a semi-solid substance.

Example 1A(iii)—SB3 (Ratio of [25% 6/2]:[75% 4/2])

1.28 g of the 1H, 1H, 2H, 2H perfluorooctyltriethoxysilane (Sigma Aldrich, 667420-25 g) and 3.1 g of 1H, 1H, 2H, 2H-Nonafluorohexyltriethoxysilane (TCI America, T2860) (1:3 molar ratios) were taken in 10 mL ethanol, to which was added 0.3 mL of KOH solution (7.4 mg/mL). The mixture was stirred at room temperature for 24 h resulting in the precipitation of a white semi-solid product. The solvent in the reaction mixture was decanted, the precipitate washed repeatedly with ethanol, then dried under vacuum overnight at 45-50° C. The crude product was then dissolved in AK-225G solvent, and then the organic layer washed three times with ddH$_2$O, dried over anhydrous magnesium sulfate, filtered, concentrated and dried under vacuum overnight at 80° C. The resulting purified product was still a semi-solid substance.

Example 1B—Characterization of Materials

Example 1B(i)—SB1 (Ratio of [75% 6/2]:[25% 4/2])

$^1$H NMR analysis for the synthetic blend SB1 F-POSS is shown in FIG. 1. $^1$H NMR in acetone-d6 (with few drops of AK-225G) showed shifts at 2.44-2.33 ppm (m, 16H) and 0.91-0.83 (m, 16H), with some minor impurity/precursor peaks between 4.5-3.5 ppm. This product was not as readily soluble in acetone+AK-225G (NMR solvent mixture) as the 4/2 F-POSS, solubility being more similar to that of the 6/2 F-POSS.

Figure 2:
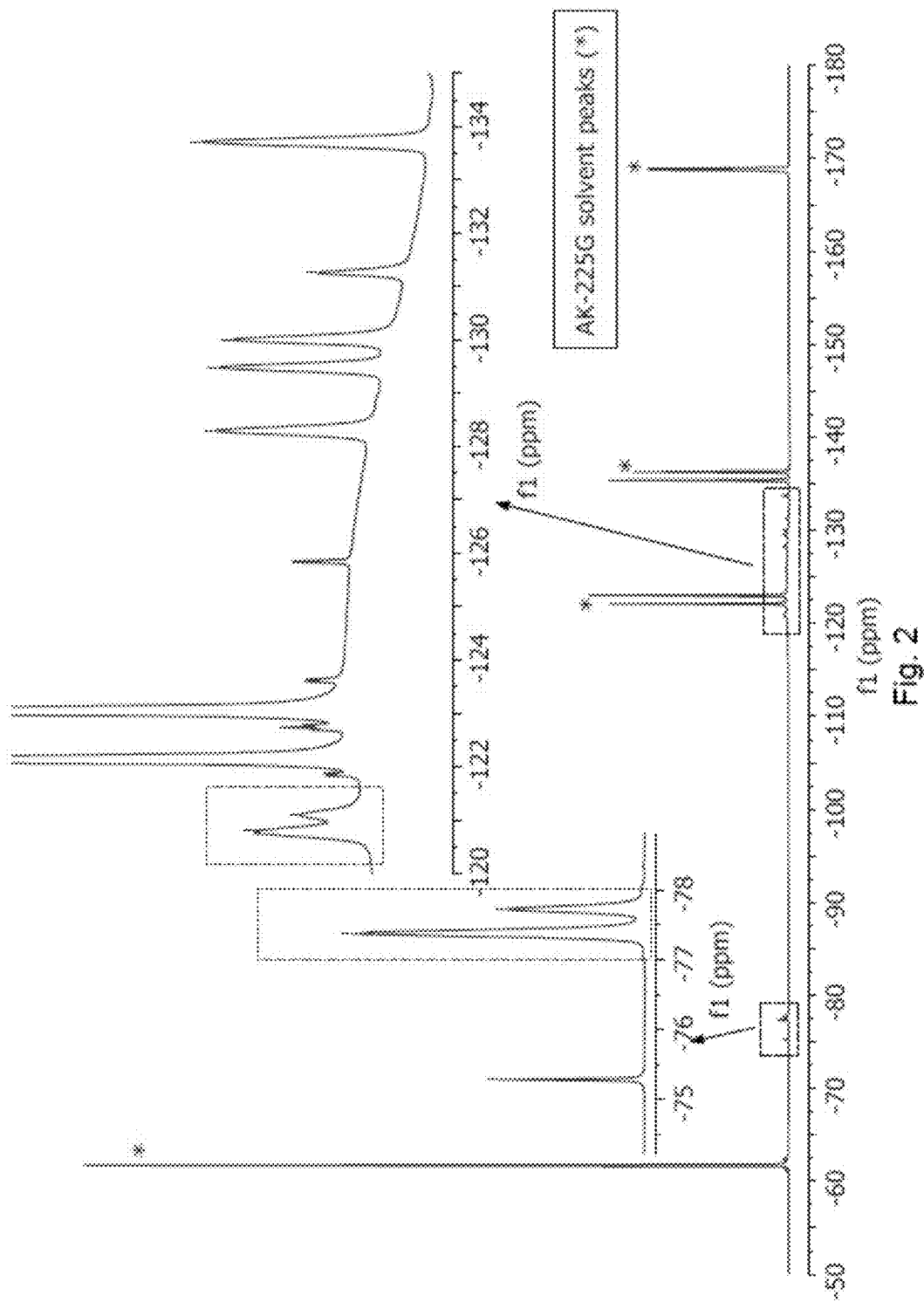
FIG. 2 is an analysis plot of $^{19}F$ NMR analysis for the synthetic blend SB1 according to Example 1A(i).

$^{19}$F NMR analysis for the synthetic blend SB1 is shown in FIG. 2. $^{19}$F NMR spectrum for SB1 showed the following chemical shifts: −77.37, −77.73, −120.80, −121.10, −128.29, −129.49, −130.01, −131.26 and −133.71. Using the spectrum for the 50/50 synthetic blend as a reference, peak assignments can be made for —CF$_2$— and —CF$_3$ groups for the two different side chains in the SB1 blend:

Peaks from 4/2 side chain: δ−77.73 (for —CF$_3$), −121.10 (for —CF$_2$—), −131.26 (for —CF$_2$—) and −133.71 (for —CF$_2$—) Peaks from 6/2 side chain: δ−77.37 (for —CF$_3$), −120.80 (for —CF$_2$—), −128.29 (for —CF$_2$—), −129.49 (for —CF$_2$—), −130.01 (for —CF$_2$—) and −133.71 (for —CF$_2$—, overlapped with the 4/2 side chain). Interestingly, as highlighted by the rectangular boxes in FIG. 2, the peak height for that at −77.37 ppm (—CF$_3$ from 6/2 side chain) is greater than that at −77.73 ppm (—CF$_3$ from 4/2 side chain). Incidentally, these two peak heights and integrations were almost 1:11 in the 50/50 blend. A similar trend is observed for the peak heights at −120.80 ppm (from 6/2 side chain) and −121.10 (from 4/2 side chain).

Figure 3:
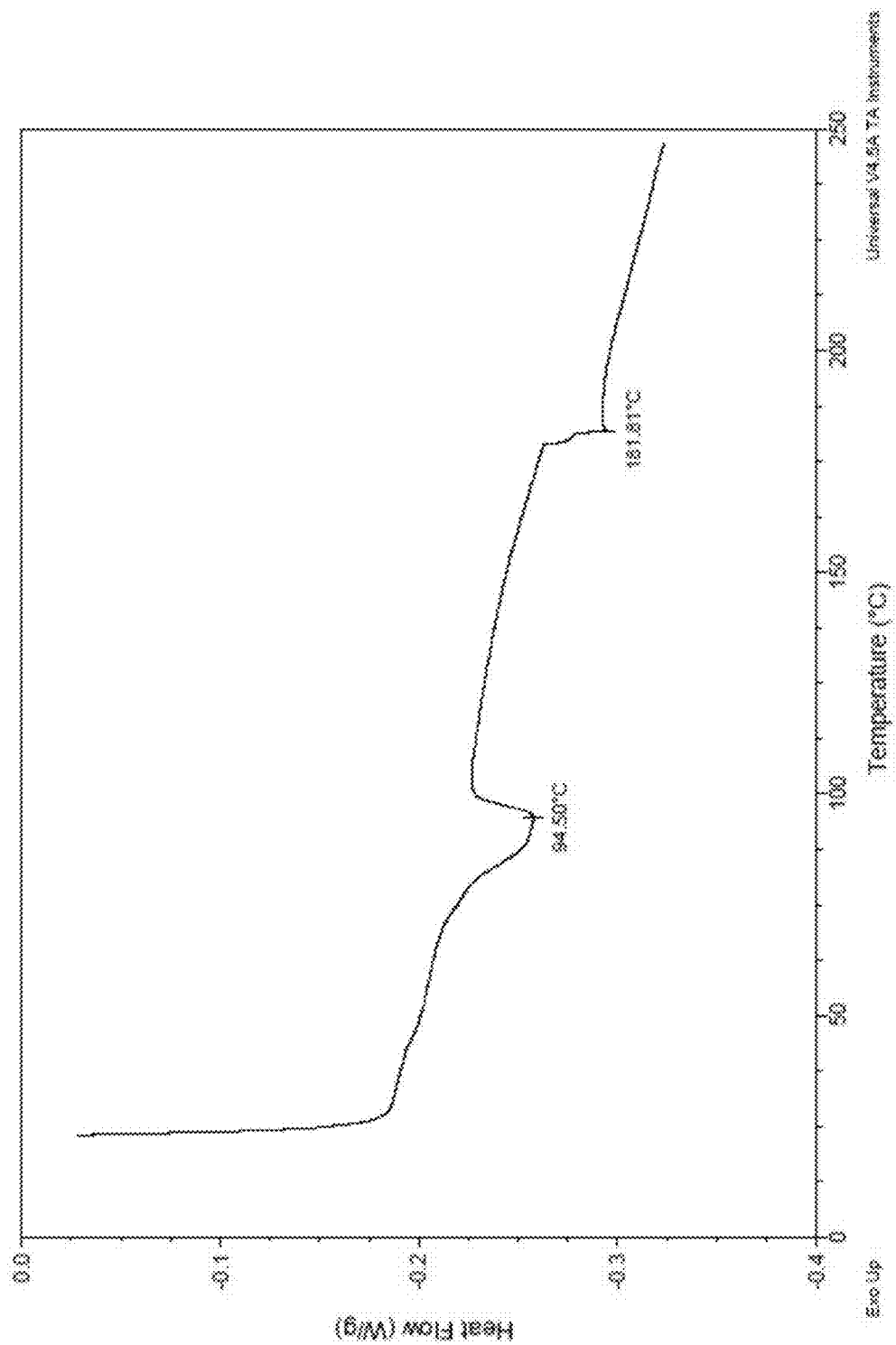
FIG. 3 is a graph of Differential Scanning Calorimetry of SB1 according to Example 1A(i).

DSC of SB1 is shown in FIG. 3. The melting points of pure 4/2 and 6/2 F-POSS are about 30° C. higher than those of SB1. The fact that the melting points of the synthetic blend F-POSS are different suggests that different compounds with different properties were chemically formed by varying the molar ratios of the precursors.

Example 1B(ii)—SB2 (Ratio of [50% 6/2]:[50% 4/2])

Figure 4:
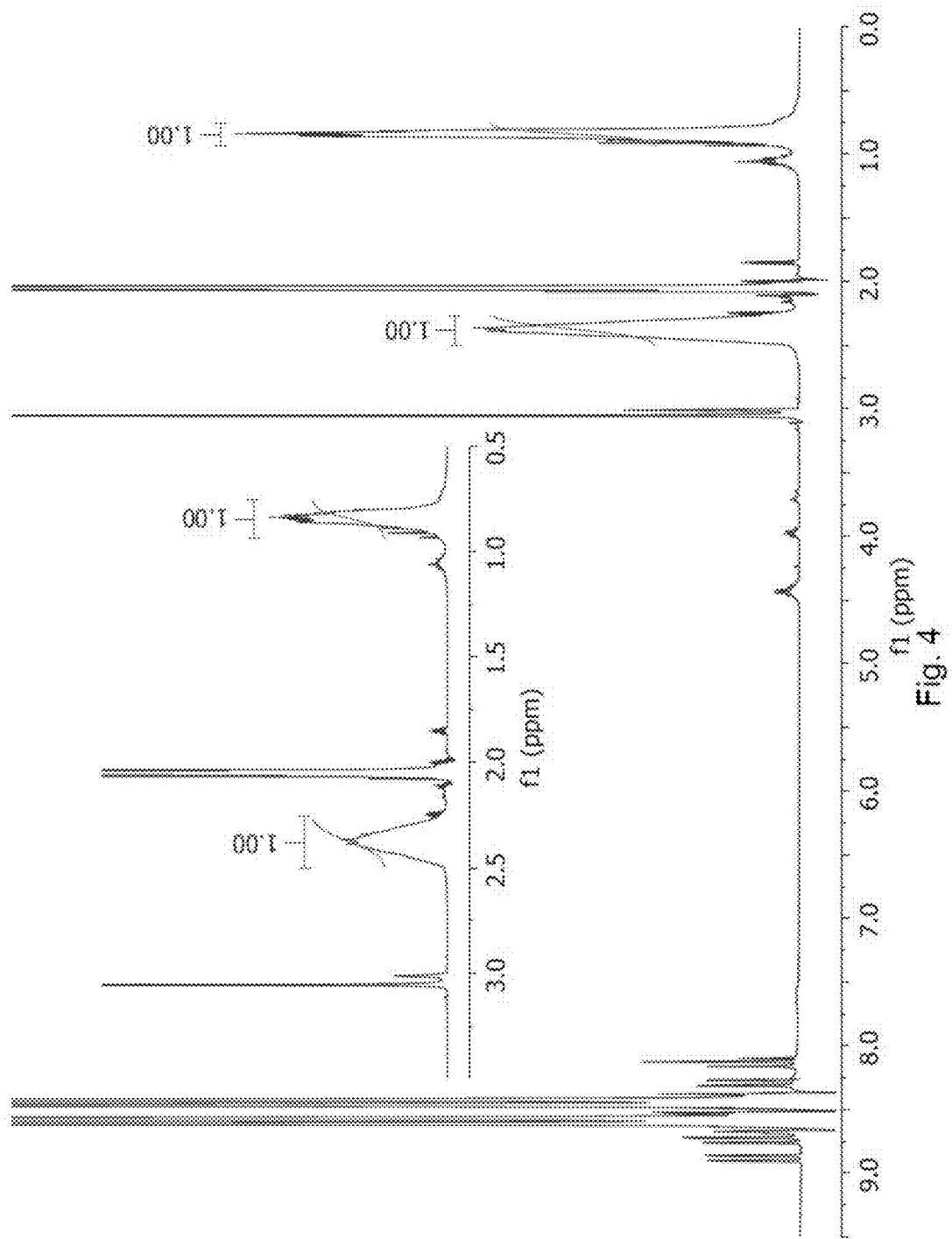
FIG. 4 is an analysis plot of $^1H$ NMR analysis for a synthetic blend SB2 according to Example 1A(ii).

$^1$H NMR analysis for the synthetic blend SB2 F-POSS is shown in FIG. 4. $^1$H NMR in acetone-d6 (with few drops of AK-225G) showed shifts at 2.39-2.34 ppm (in, 16H) and 0.89-0.82 (m, 16H), with some minor impurity/precursor peaks between 4.5-3.5 ppm. This product was more readily soluble in acetone+AK-225G (NMR solvent mixture) than the 75%-25% 6/2-4/2 blend (203-64-1).

Figure 5:
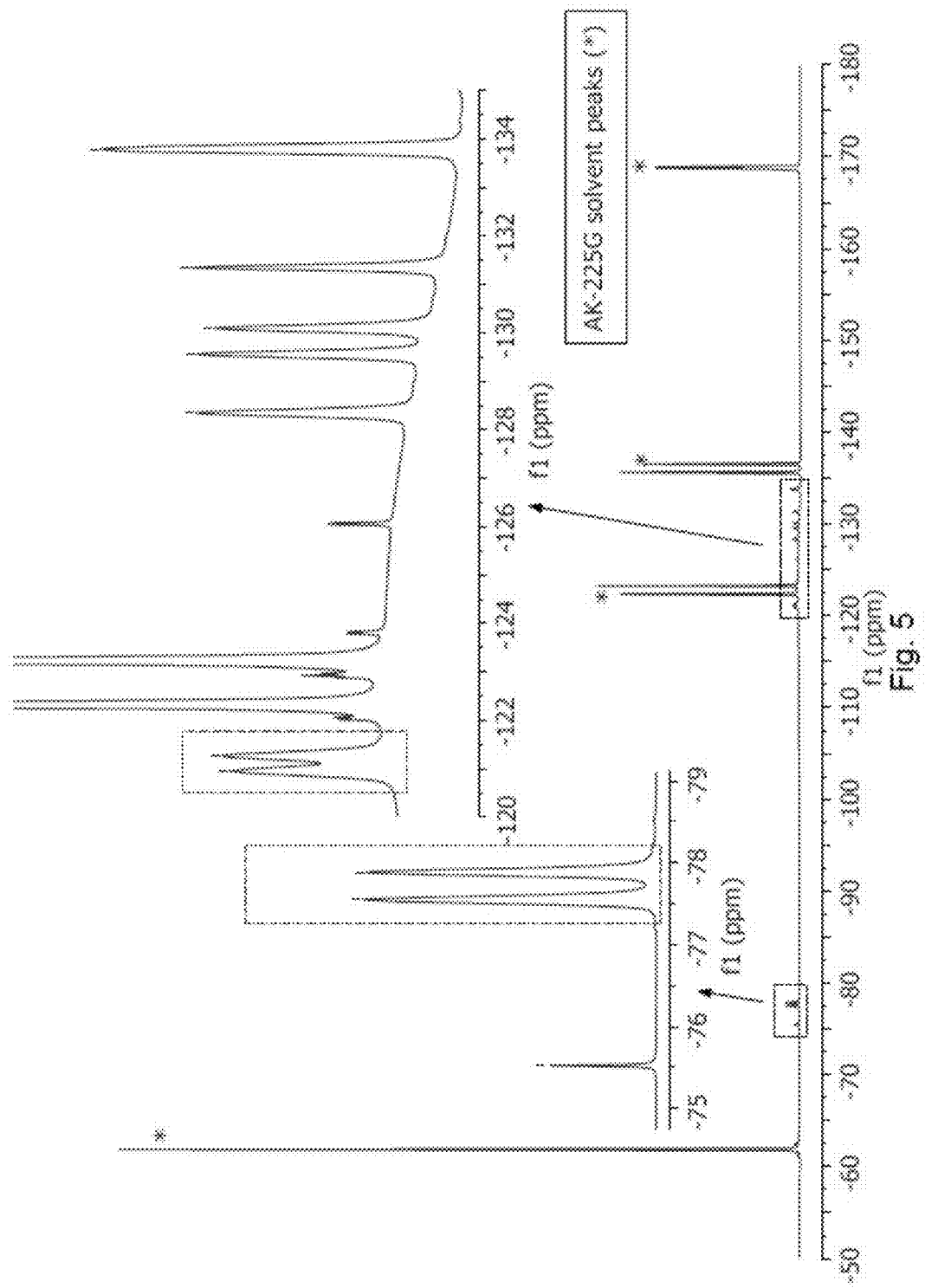
FIG. 5 is an $^{19}F$ NMR analysis for the synthetic blend SB2 according to Example 1A(ii).

$^{19}$F NMR analysis for the synthetic blend SB2 F-POSS is shown in FIG. 5. $^{19}$F NMR spectrum for SB2 showed the following chemical shifts: −77.55, −77.88, −120.96, −121.27, −128.35, −129.56, −130.09, −131.35 and −133.79. The integrations for the peaks at −77.55 and −77.88 ppm (highlighted by a blue rectangle in the figure above), which showed very similar peak heights, were obtained at the ratio of approx. 1:1. This suggests that these two peaks each represent the —$CF_3$ groups on the 6/2 and the 4/2 side chains, the peak assignments based on the positioning of the —$CF_3$ peaks in the pure 6/2 and 4/2 F-POSS materials and their precursors. Similarly, the two peaks at −120.96 and −121.27 ppm (also highlighted by a rectangle in FIG. 5) have very similar peak heights, and can be assigned to one each of the 6/2 and the 4/2 F-POSS.

Figure 6:
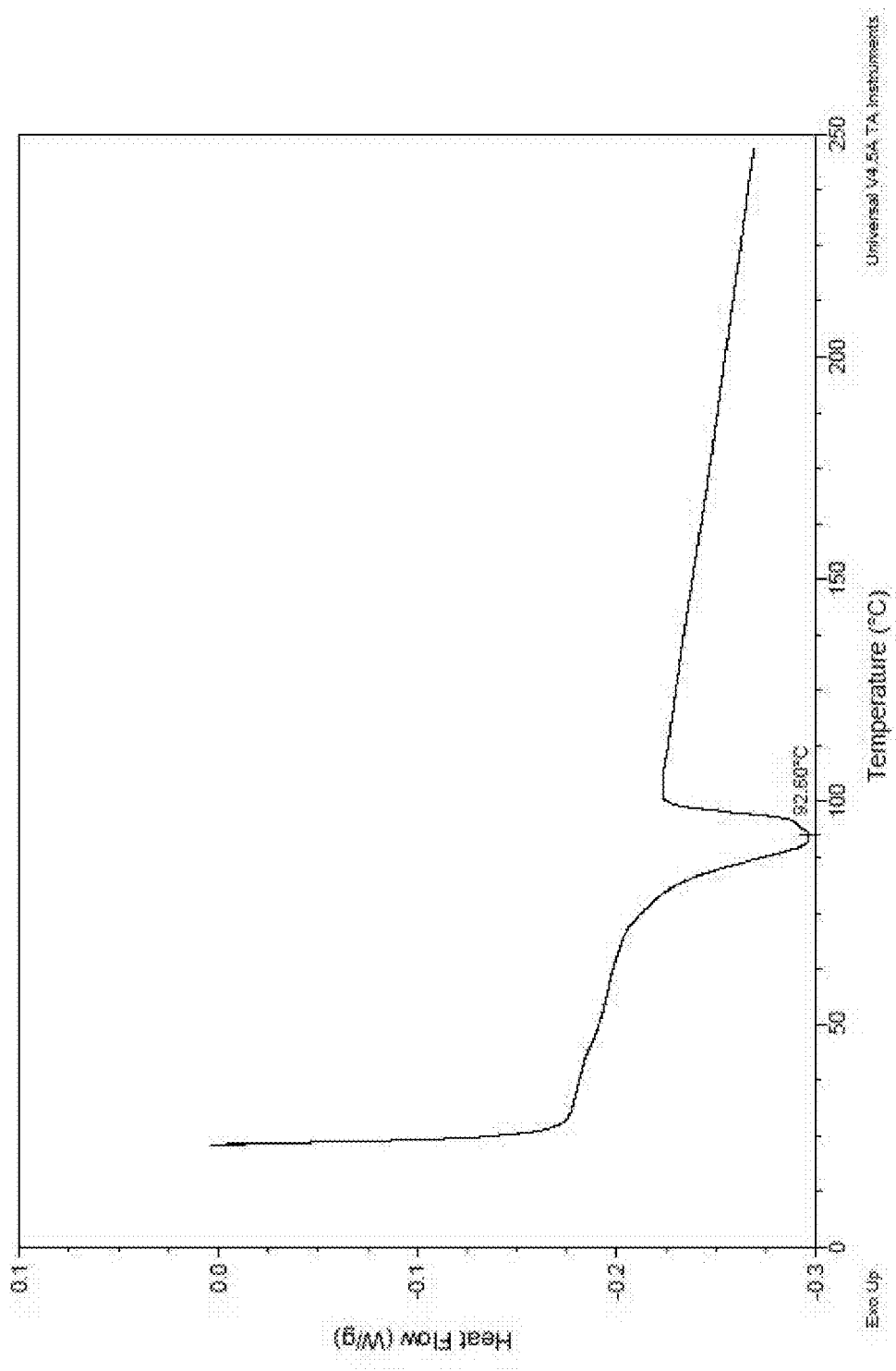
FIG. 6 is a graph of Differential Scanning Calorimetry of SB2 according to Example 1A(ii).

DSC of SB2 is shown in FIG. 6. The melting points of pure 4/2 and 6/2 F-POSS are about 30° C. higher than those of the synthetic blend SB2. The fact that the melting points of the synthetic blend F-POSS are different suggests that different compounds with different properties were chemically formed by varying the molar ratios of the precursors.

Example 1B(iii)—SB3 (Ratio of [25% 6/2]:[75% 4/2])

Figure 7:
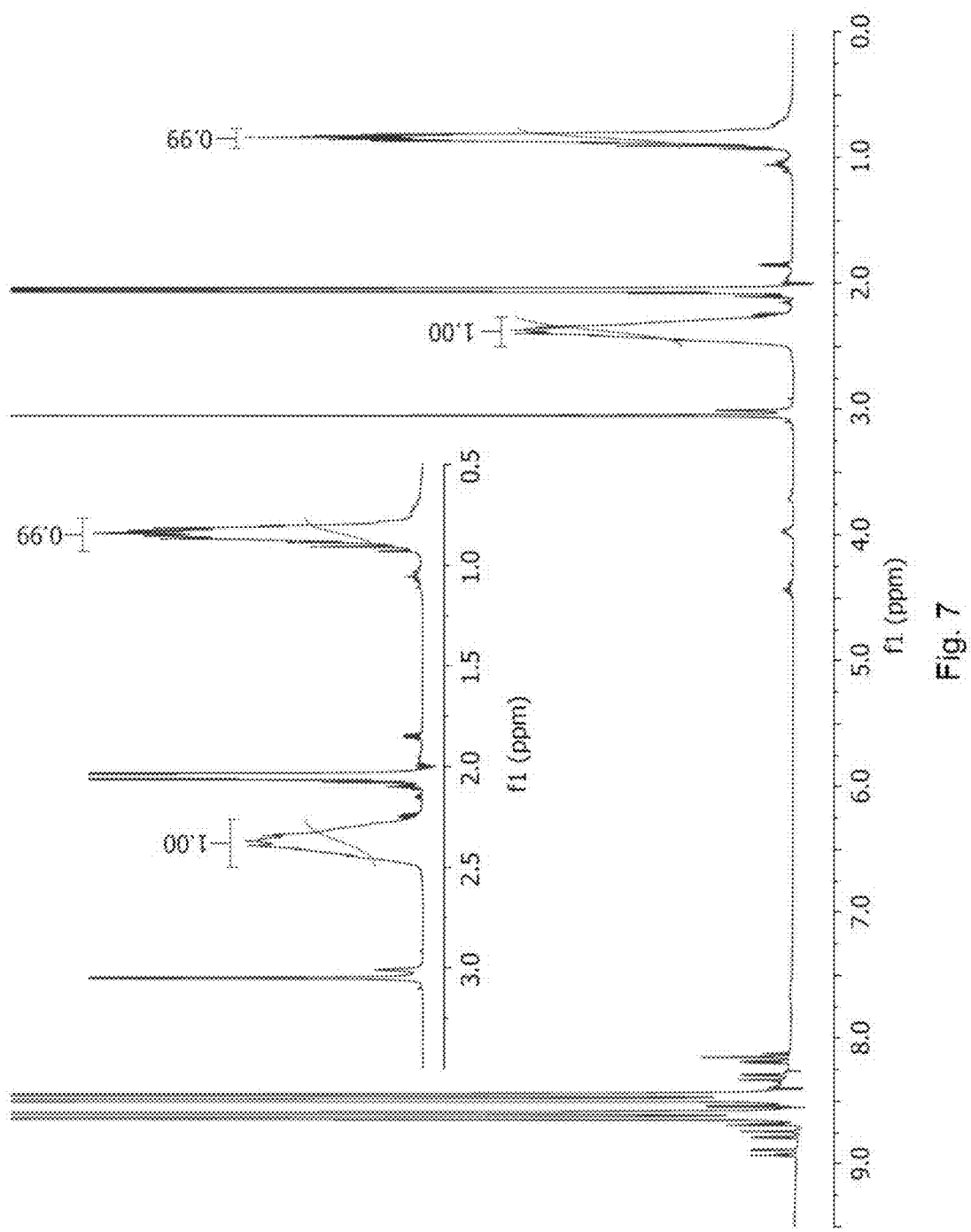
FIG. 7 is an analysis plot of $^1H$ NMR analysis for a synthetic blend SB3 according to Example 1A(iii).

$^1$H NMR analysis for the synthetic blend SB3 F-POSS is shown in FIG. 7. $^1$H NMR in acetone-d6 (with few drops of AK-225G) showed shifts at 2.45-2.34 ppm (m, 16H) and 0.91-0.80 (m, 16H), with slight impurity/precursor peaks between 4.5-3.5 ppm. This product was readily soluble in acetone+AK-225G (NMR solvent mixture), solubility being very similar to that of the 4/2 F-POSS.

Figure 8:
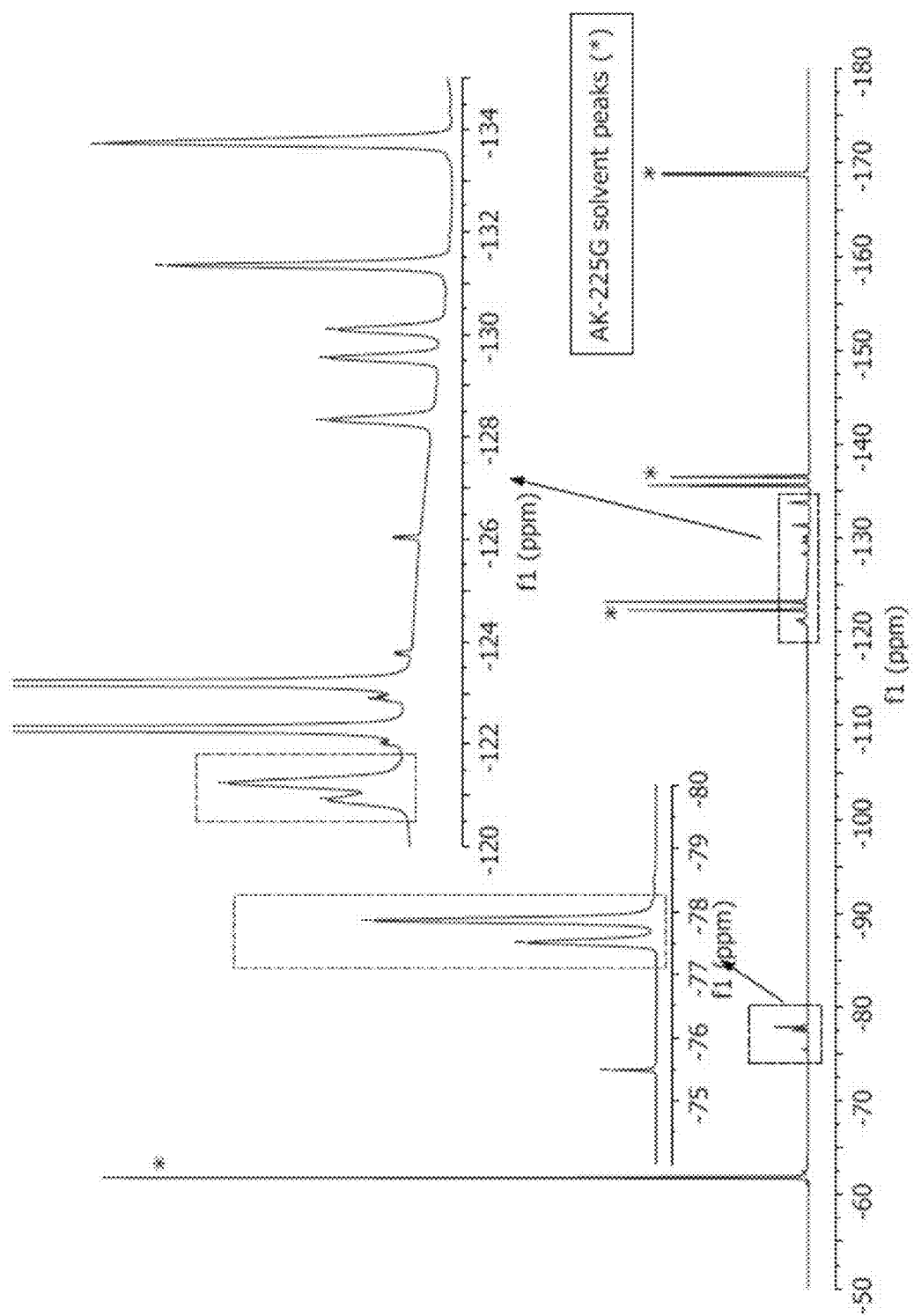
FIG. 8 is an analysis plot of $^{19}F$ NMR analysis for the synthetic blend SB3 according to Example 1A(iii).

$^{19}$F NMR analysis for the synthetic blend SB3 F-POSS is shown in FIG. 8. $^{19}$F NMR spectrum for the synthetic blend SB3 showed the following chemical shifts: −77.51, −77.86, −120.94, −121.24, −128.34, −129.55, −130.10, −131.35 and −133.74. Using the spectrum for the 50/50 synthetic blend as a reference, peak assignments can be made for —$CF_2$— and —$CF_3$ groups for the two different side chains in the 75/25 blend:

Peaks from 4/2 side chain: δ−77.86 (for —$CF_3$), −121.24 (for —$CF_2$—), −131.35 (for —$CF_2$—) and −133.74 (for —$CF_2$—) Peaks from 6/2 side chain: δ−77.51 (for —$CF_3$), −120.94 (for —$CF_2$—), −128.34 (for —$CF_2$—), −129.55 (for —$CF_2$—), −130.10 (for —$CF_2$—) and −133.74 (for —$CF_2$—, overlapped with the 4/2 side chain) Interestingly, as highlighted by the rectangular boxes in the figure above, the peak height for that at −77.51 ppm (—$CF_3$ from 6/2 side chain) is smaller than that at −77.86 ppm (—$CF_3$ from 4/2 side chain). Incidentally, these two peak heights and integrations were almost 1:1 in the 50/50 blend. A similar trend is Observed for the peak heights at −120.94 ppm (from 6/2 side chain) and −121.24 (from 4/2 side chain).

Figure 9A:
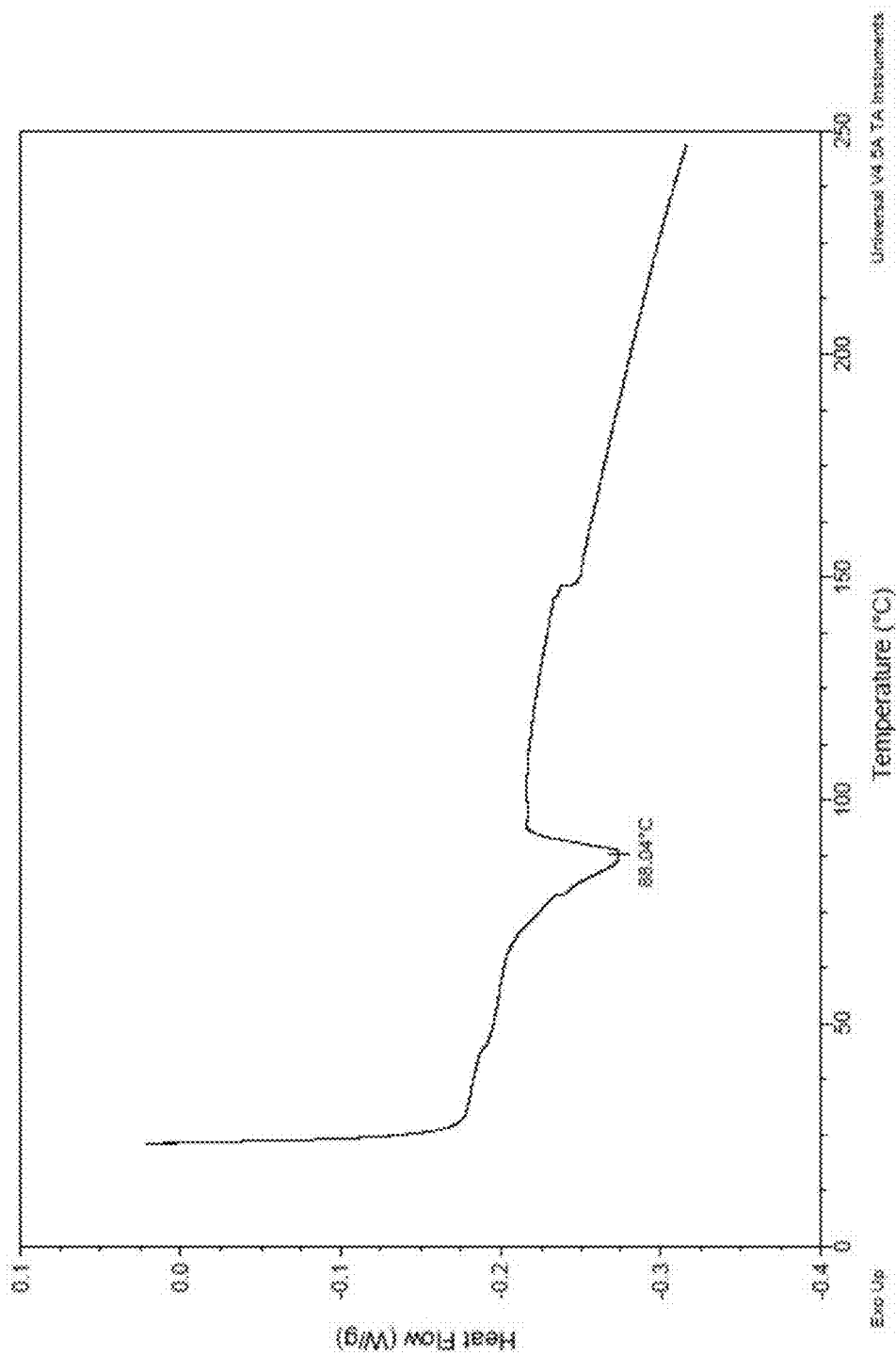
FIG. 9A is a graph of a first Differential Scanning Calorimetry analysis of SB3 prepared according to Example 1B(iii).
Figure 9B:
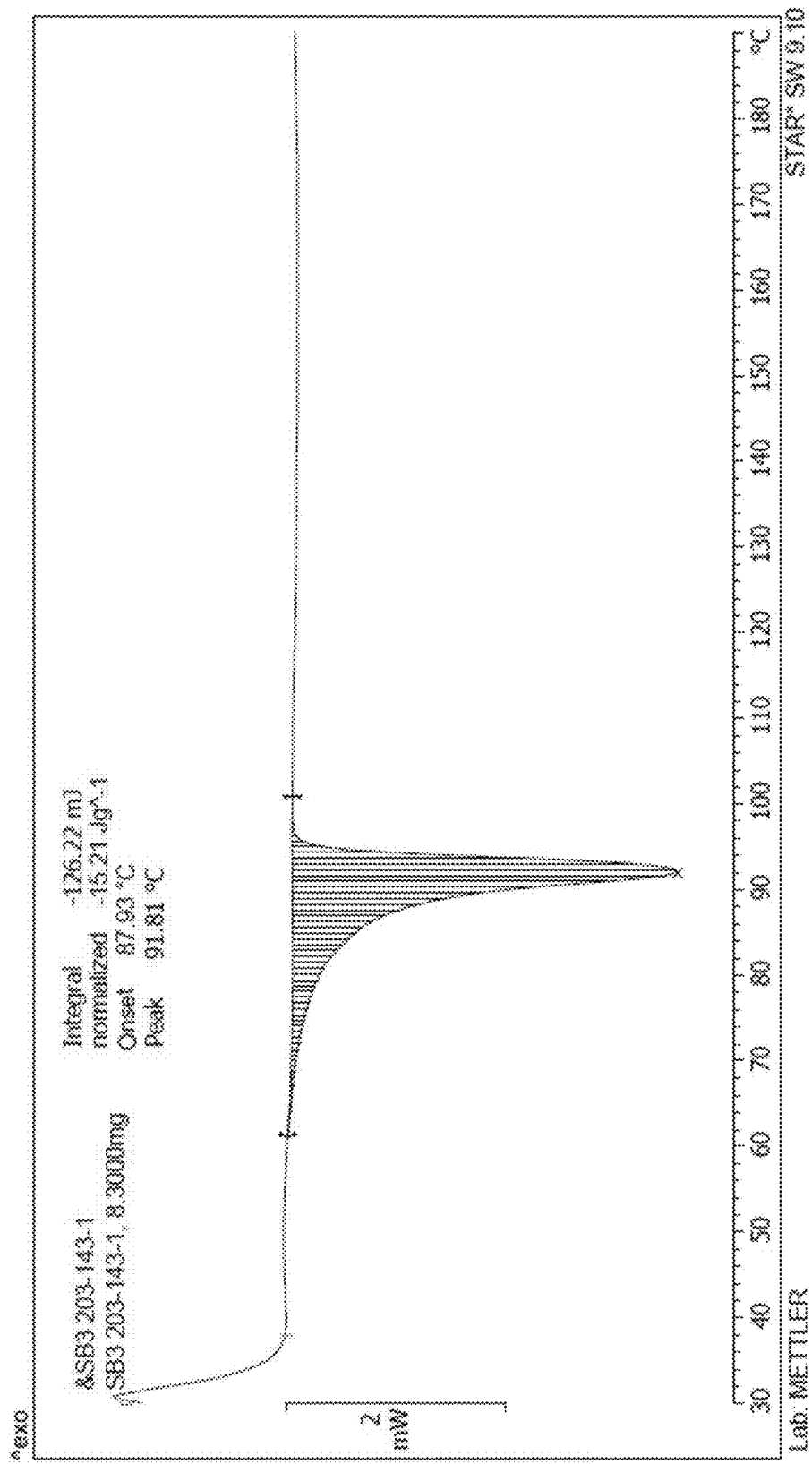
FIG. 9B is a graph of a second Differential Scanning Calorimetry analysis of SB3 prepared according to Example 1B(iii).

DSC of SB3 is shown in FIGS. 9A and 9B. The melting points of pure 4/2 and 6/2 F-POSS are about 30° C. higher than those of the synthetic blends SB3. The fact that the melting points of the synthetic blend F-POSS are different suggests that different compounds with different properties were chemically formed by varying the molar ratios of the precursors.

Example 1C—Comparison of 6/2:4/2 Synthetic Blends

Figure 10:
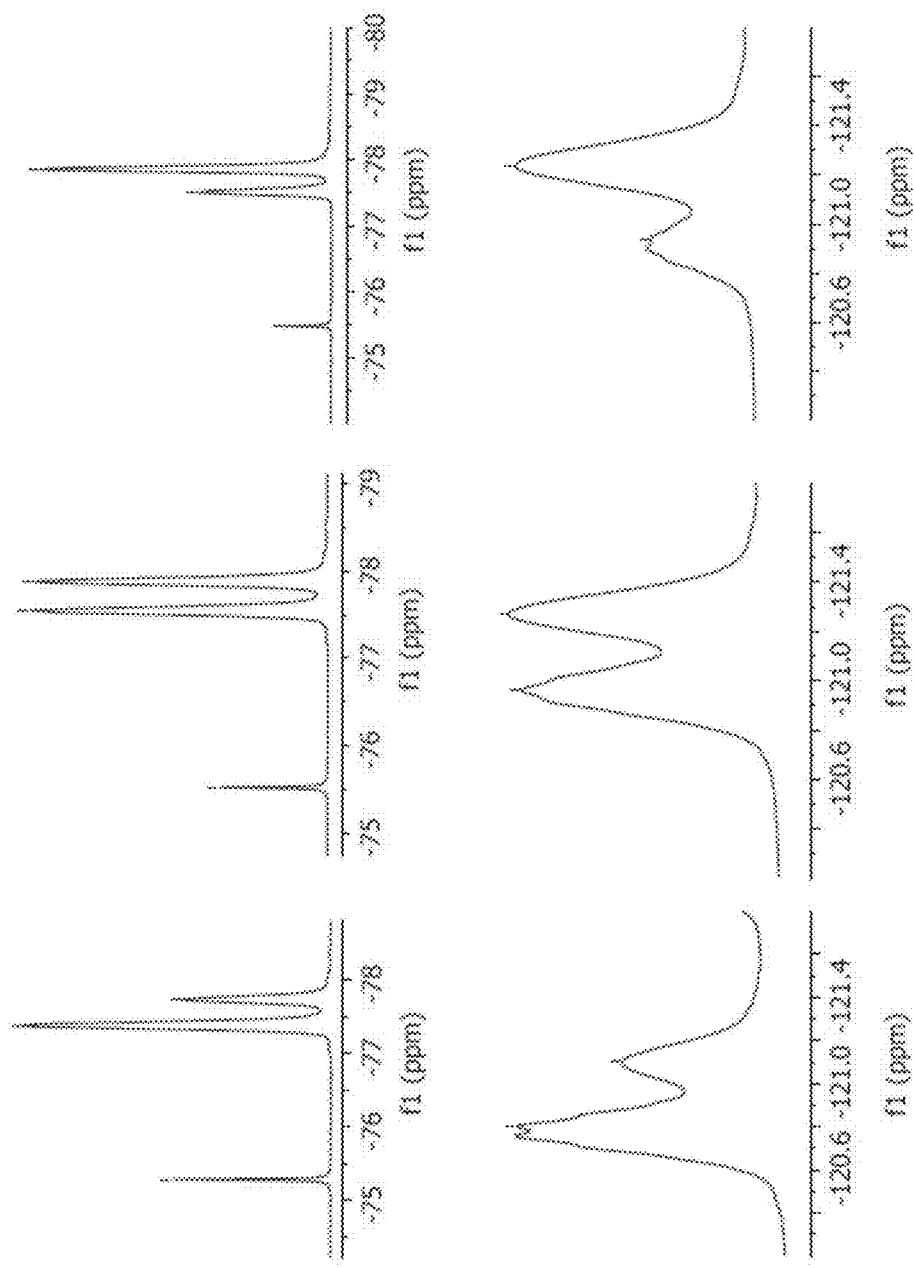
FIG. 10 is an analysis plot $^{19}$F NMR analysis comparing the synthetic blends SB1, SB2 and SB3 of Examples 1A(i), 1A(ii) and 1A(iii).

Example 1C(i)—19F NMR $^{19}$F NMR analysis comparing the synthetic blends SB1, SB2 and SB3 F-POSS is shown in FIG. 10. The changing peak heights for the two sets of peaks (highlighted above) in the three synthetic blends are shown in FIG. 10. Although peaks for the SB1 and the SB3 synthetic blends could not be integrated due to skewed baselines, the trend is clear from the figure below suggesting a decrease in the percentage of the 6/2 side chains with an increase in the percentage for the 4/2 side chains.

Example 1C(ii)—Melting Points

Figure 11:
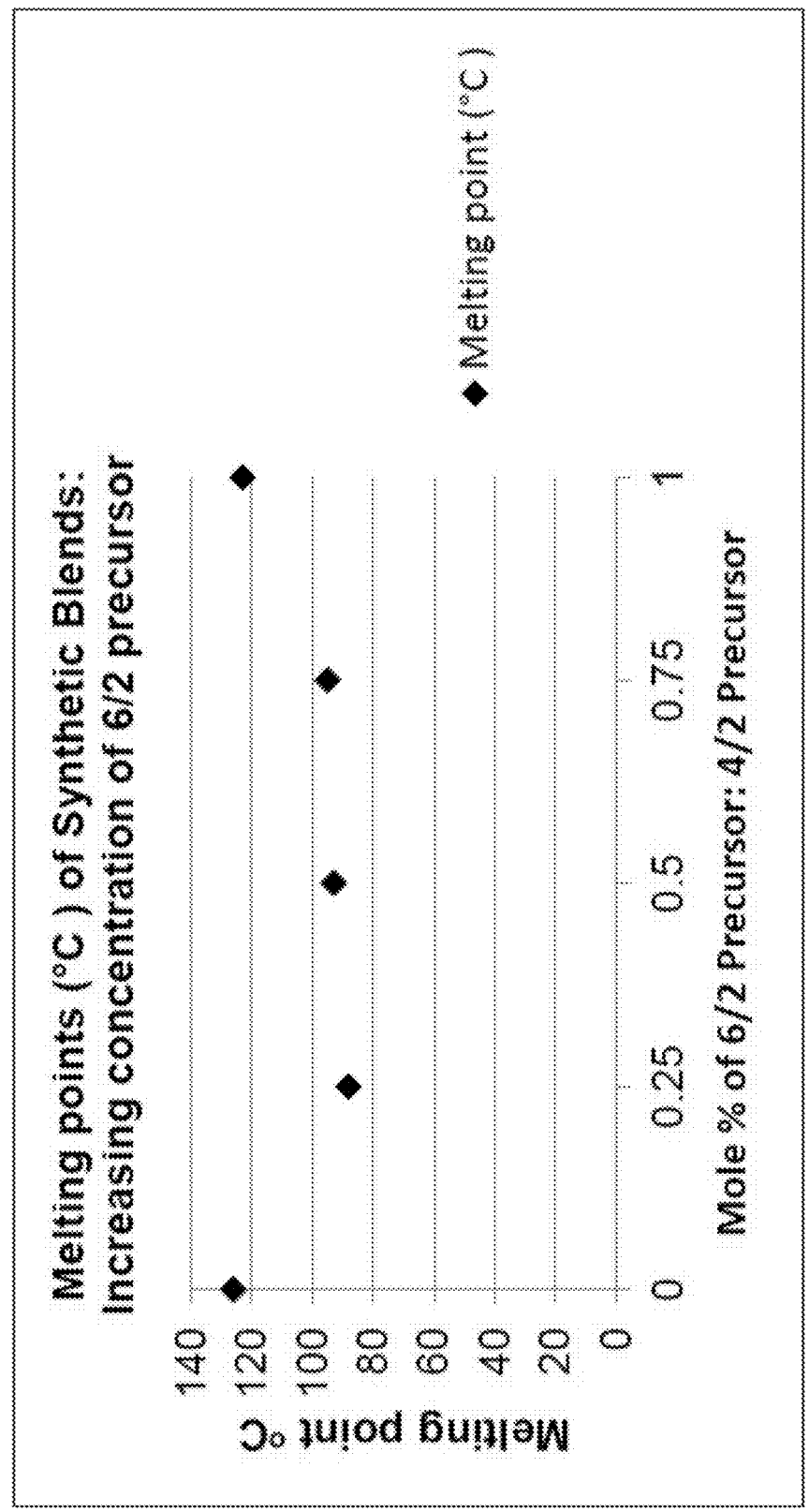
FIG. 11 is a graph of the melting points (in ° C.) of synthetic blends.

Table 1 below and FIG. 11 show the difference in melting temperatures for the various synthetic blend materials.

TABLE 1

| Compound (F-POSS precursor) | Mole Ratio of 6/2:4:2 precursor | Melting point (° C.) |
| --- | --- | --- |
| 6/2 F-POSS | 1 | 128 |
| SB1: 6/2:4/2 (75/25) F-POSS | 0.75 | 95 |
| SB2: 6/2:4/2 (50/50) F-POSS | 0.5 | 93 |
| SB3: 6/2:4/2 (25/75) F-POSS | 0.25 | 92 |
| 4/2 F-POSS | 0 | 126 |

Example 1D—Percent Composition Based on Feedstock

Figure 12:
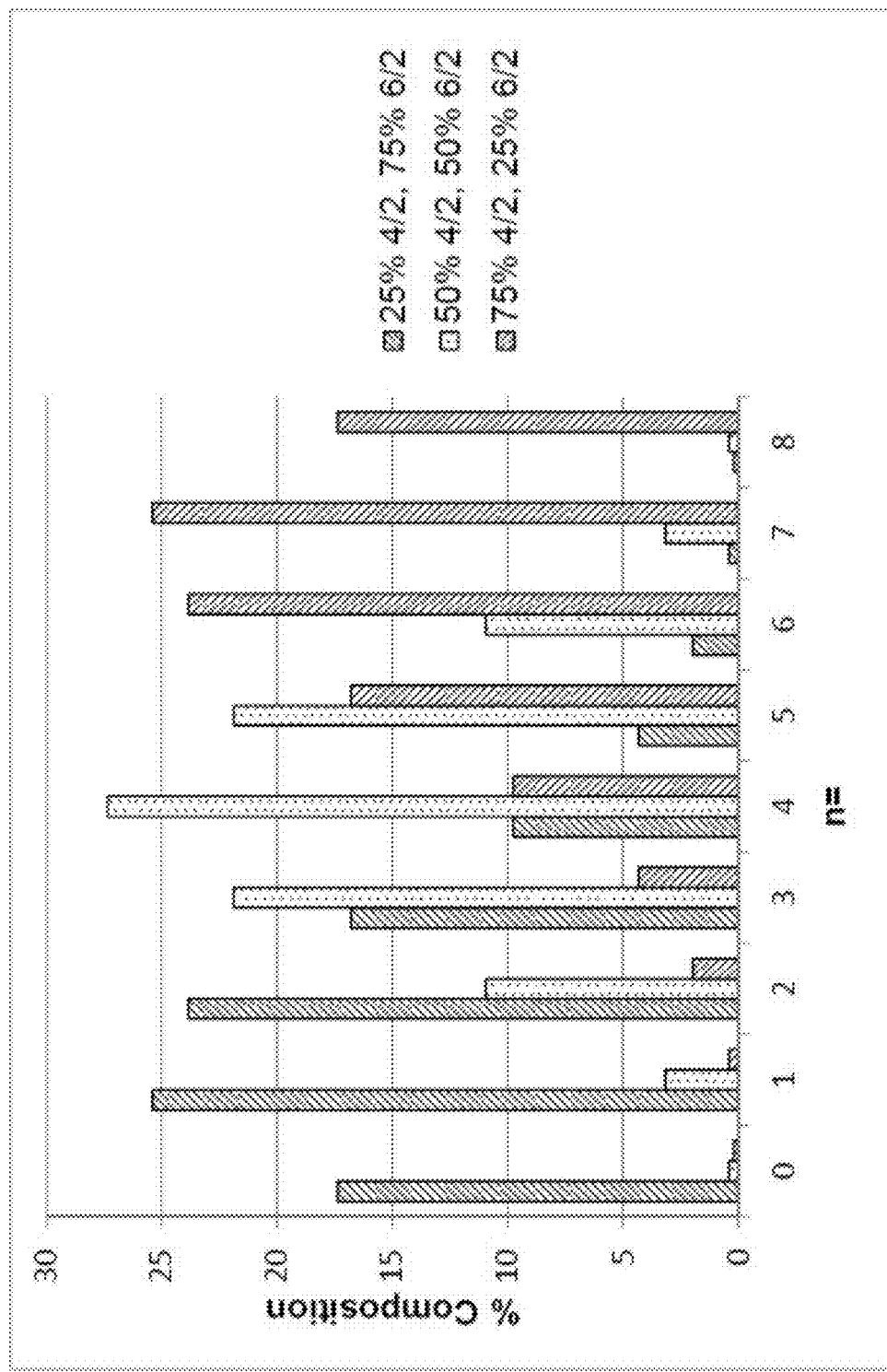
FIG. 12 is a chart of the approximate percent composition of SB1, SB2 and SB3 as prepared based on feedstock.

The approximate percent composition of SB1, SB2 and SB3 as prepared above, based on the feedstock, is shown in Table 2 below and in FIG. 12.

TABLE 2

| | | Approximate Percent Composition Based on Feedstock | | | | | | | | |
| --- | --- | --- | --- | --- | --- | --- | --- | --- | --- | --- |
| | n = | 0 | 1 | 2 | 3 | 4 | 5 | 6 | 7 | 8 |
| SB1 | 25% 4/2, 75% 6/2 | 17.383 | 25.391 | 23.828 | 16.797 | 9.766 | 4.297 | 1.953 | 0.391 | 0.195 |
| SB2 | 50% 4/2, 50% 6/2 | 0.391 | 3.125 | 10.938 | 21.875 | 27.344 | 21.875 | 10.938 | 3.125 | 0.391 |
| SB3 | 75% 4/2, 50% 6/2 | 0.195 | 0.391 | 1.953 | 4.297 | 9.766 | 16.797 | 23.828 | 25.391 | 17.383 |

Example 2—Formulation of Synthetic Blends in Paint

Two-component paint was prepared according to manufacturer's directions by mixing Windmastic TopCoat Repair Kit 7035 Grey Part A base paint (Carboline, UN1293) with Windmastic TopCoat Repair Kit Part B Resin (Carboline, UN1866) 6:1 (v/v). To ensure accurate measurements of paint, six volumes (mLs) of Part A were weighed several times and the weights averaged 8.6 g; one volume (mL) of Part B was weighed several times averaging 0.97 g. Weight-to-weight ratios were then used throughout each experiment for the formulation of the control paint. The 2 component paint (8.6 g of Part A and 0.97 g of Part B) were added to a Flacktek Speedmixer 10 mL polypropylene translucent container. The paint was then mixed for 10 minutes at 2700 rpm in the Flacktek DAC400 FVZ Speedmixer.

Approximately 0.1 g of SB1, SB2 and SB3 were weighed into 10 mL Speedmixer polypropylene containers. Paint was added to the container such that the final concentration (weight %) of synthetic blend F-POSS was 1%, 5%, 10% or 25% in the paint. The containers, including the paint only control, were then placed into the Flacktek Speedmixer for 10 minutes at 2700 rpm.

Each formulation was then coated onto 4"×4" QPanel 0.32" Dull matte finish steel plates (Guardco) using a 4 mil coating bar. The plates were dried overnight at room temperature. No unusual coating properties were observed with any of the synthetic blend formulations in paint, and perhaps offered better film forming properties.

Representative images of coated steel containing the synthetic blend SB3 at each weight % loading in paint are shown in FIGS. 13A-D (FIG. 13A—1 wt %; FIG. 13B—5 wt %; FIG. 13C—10 wt %; and FIG. 13D—25 wt %).

Example 3—Performance of Synthetic Blends in Paint

Figure 14:
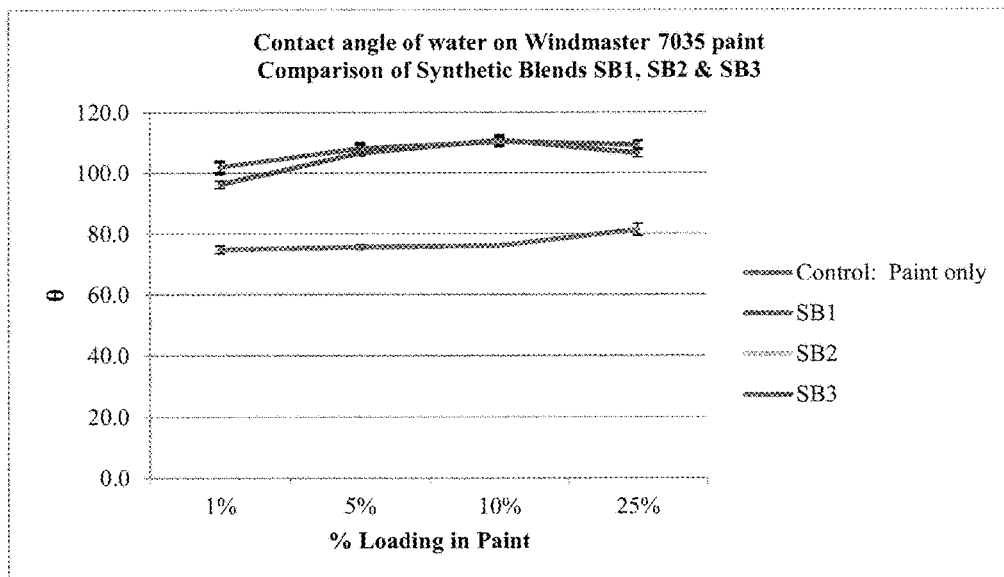
FIG. 14 is a graph of the contact angle of water of synthetic blends SB1, SB2 and SB3 on Windmaster 7035 paint.
Figure 15:
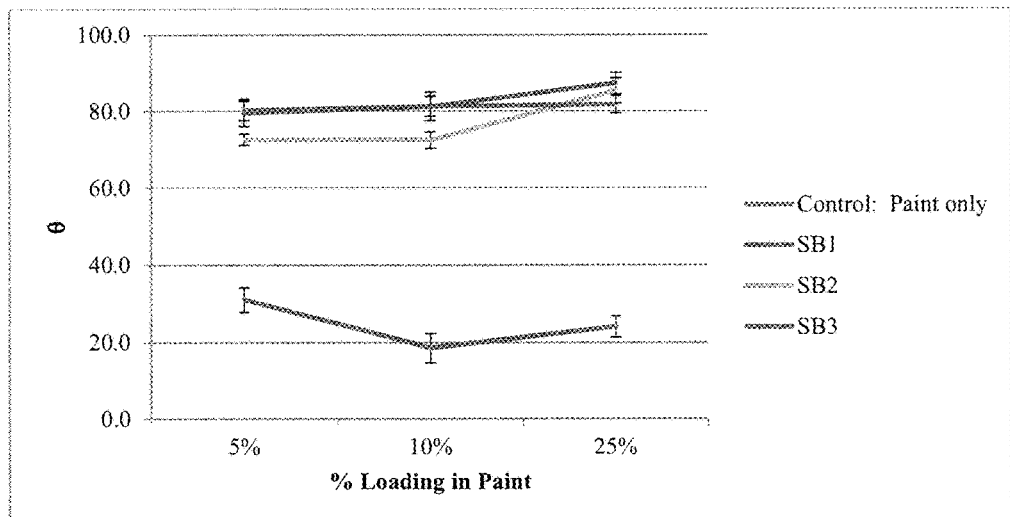
FIG. 15 is a graph of the contact angle of hexadecane of synthetic blends SB1, SB2 and SB3 on Windmaster 7035 paint.

Contact angles of water were measured using a Krauss DSA100S drop shape analyzer with an automatic syringe dispenser in 5 µL volumes FIG. 14 shows plots of the water contact angle of paint only, and of SB1, SB2 and SB3. Contact angles of hexadecane, shown in FIG. 15, were measured using the same instrument fitted with a manual syringe dispensing similar volumes.

SB1, SB2 and SB3 performed significantly better than the control of paint alone. There was no significant difference observed between the synthetic blends. The synthetic blends performed equally as well as 6/2 F-POSS or 4/2 F-POSS individually, even at 1% (wt) loading in paint. Results of the synthetic blends show significant increases in hexadecane contact angles compared to 6/2 F-POSS or 4/2 F-POSS alone.

Figure 16:
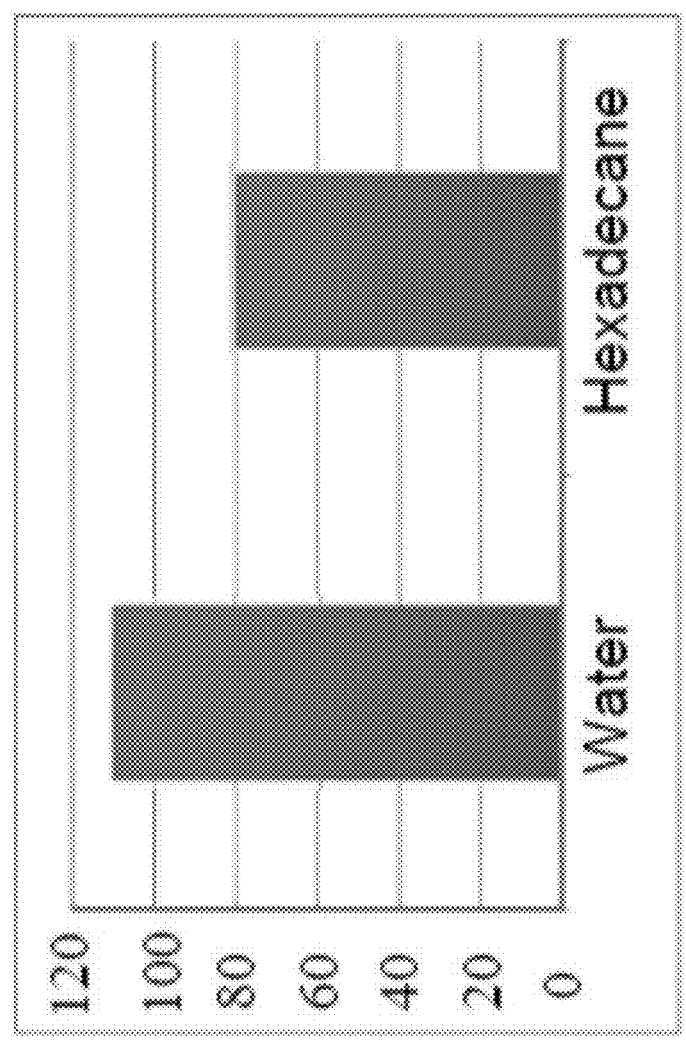
FIG. 16 is a graph of the contact angles of water and hexadecane of synthetic blend SB3 in 50/50% blends of PEMA on glass substrates with 1% weight loadings in AK-225.

FIG. 16 is a graph of the contact angle of water (110 degrees) and the contact angle of hexadecane (80 degrees) of synthetic blend SB3 in 50/50% blends of PEMA on glass substrates with 1% weight loadings in AK-225.

Although only a number of exemplary embodiments have been described in detail above, those skilled in the art will readily appreciate that many modifications are possible in the exemplary embodiments without materially departing from the novel teachings and advantages. Accordingly, all such modifications are intended to be included within the scope of this disclosure as defined in the following claims.

While the methods, equipment and systems have been described in connection with specific embodiments, it is not intended that the scope be limited to the particular embodiments set forth, as the embodiments herein are intended in all respects to be illustrative rather than restrictive.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect.

As used in the specification and the appended claims, the singular forms a "an" and "the" include plural referents unless the context clearly dictates otherwise.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. The word "exemplary" or "illustrative" means "an example of" and is not intended to convey an indication of a preferred or ideal embodiment. "Such as" is not used in a restrictive sense, but for explanatory purposes.

Disclosed are components that can be used to perform the disclosed methods, equipment and systems. These and other components are disclosed herein, and it is understood that when combinations, subsets, interactions, groups, etc., of these components are disclosed that while specific reference of each various individual and collective combinations and permutation of these may not be explicitly disclosed, each is specifically contemplated and described herein, for all methods, equipment and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

It should further be noted that any patents, applications and publications referred to herein are incorporated by reference in their entirety.

What is claimed is:

1. A synthetic blend composition comprising:
a distribution of molecules produced by a process comprising mixing a first feedstock and a second feedstock, wherein the first feedstock comprises a first fluorinated triethoxysilane and the second feedstock comprises a second fluorinated triethoxysilane that is different from the first fluorinated triethoxysilane, and
wherein each of the molecules of the distribution of molecules has a matrix structure having eight apices.

2. The synthetic blend composition of claim 1, wherein the first fluorinated triethoxysilane is of the formula $R^1Si(OR^A)_3$, wherein $R^1$ is a long-chain fluorinated alkyl having a carbon chain length of $C_1x$, where x is a range of 4-10, and each $R^A$ is independently $C_1$-$C_6$ alkyl.

3. The synthetic blend composition of claim 2, wherein the second fluorinated triethoxysilane is of the formula $R^2Si(OR^B)_3$, wherein $R^2$ is a long-chain fluorinated alkyl having a carbon chain length of $C_2y$, where y is a range of 4-10, and each $R^B$ is independently $C_1$-$C_6$ alkyl.

4. The synthetic blend composition of claim 3, wherein a first portion of the distribution of molecules has a $C_{1x}:C_{2y}$ ratio of 1:0, a second portion of the distribution of molecules has a $C_{1x}:C_{2y}$ ratio of 0:1, and a third portion of the distribution of molecules has a $C_{1x}:C_{2y}$ ratio in the range of from 1:7 to 7:1.

5. The synthetic blend composition of claim 1, wherein the first fluorinated triethoxysilane comprises a fluorinated alkyl group selected from the group consisting of 4/2 fluorinated alkyl, 3/3 fluorinated alkyl, 6/2 fluorinated alkyl, 4/4 fluorinated alkyl, 8/2 fluorinated alkyl and 6/4 fluorinated alkyl.

6. The synthetic blend composition of claim 5, wherein the second fluorinated triethoxysilane comprises a fluorinated alkyl group selected from the group consisting of 3/3 fluorinated alkyl, 6/2 fluorinated alkyl, 4/4 fluorinated alkyl, 8/2 fluorinated alkyl and 6/4 fluorinated alkyl.

7. The synthetic blend composition of claim 6, wherein the fluorinated alkyl group of the first fluorinated triethoxysilane is 4/2 fluorinated alkyl.

8. The synthetic blend composition of claim 7, wherein the fluorinated alkyl group of the second fluorinated triethoxysilane is 6/2 fluorinated alkyl.

9. The synthetic blend composition of claim 1, wherein the distribution of molecules is a Gaussian distribution.

10. A method of forming an F-POSS synthetic blend material having a distribution of apex substituents, comprising:
   a. providing a first feedstock comprising a first fluorinated triethoxysilane;
   b. providing a second feedstock comprising a second fluorinated triethoxysilane that is different from the first fluorinated triethoxysilane; and
   c. reacting the first feedstock with the second feedstock under conditions so as to form a distribution of molecules, each molecule of the distribution of molecules comprising a matrix structure having eight apices.

11. The method of claim 10, wherein the first fluorinated triethoxysilane is of the formula $R^1Si(OR^A)_3$, wherein $R^1$ is a long-chain fluorinated alkyl having a carbon chain length of $C_1x$, where x is a range of 4-10, and each $R^A$ is independently $C_1$-$C_6$ alkyl.

12. The method of claim 11, wherein the second fluorinated triethoxysilane is of the formula $R^2Si(OR^B)_3$, wherein $R^2$ is a long-chain fluorinated alkyl having a carbon chain length of $C_2y$, where y is a range of 4-10, and each $R^B$ is independently $C_1$-$C_6$ alkyl.

13. The method of claim 12, wherein a first portion of the distribution of molecules has a $C_{1x}$:$C_{2y}$ ratio of 1:0, a second portion of the distribution of molecules has a $C_{1x}$:$C_{2y}$ ratio of 0:1, and a third portion of the distribution of molecules has a $C_{1x}$:$C_{2y}$ ratio in the range of from 1:7 to 7:1.

14. The method of claim 10, wherein the first fluorinated triethoxysilane comprises a fluorinated alkyl group selected from the group consisting of 4/2 fluorinated alkyl, 3/3 fluorinated alkyl, 6/2 fluorinated alkyl, 4/4 fluorinated alkyl, 8/2 fluorinated alkyl and 6/4 fluorinated alkyl.

15. The method of claim 14 wherein the second fluorinated triethoxysilane comprises a fluorinated alkyl group selected from the group consisting of 3/3 fluorinated alkyl, 6/2 fluorinated alkyl, 4/4 fluorinated alkyl, 8/2 fluorinated alkyl and 6/4 fluorinated alkyl.

16. The method of claim 15, wherein the fluorinated alkyl group of the first fluorinated triethoxysilane is 4/2 fluorinated alkyl.

17. The method of claim 16, wherein the fluorinated alkyl group of the second fluorinated triethoxysilane is 6/2 fluorinated alkyl.

18. The method of claim 10, wherein the distribution of molecules is a Gaussian distribution.

19. A paint composition comprising the synthetic blend composition of claim 1 and at least one polymer base paint material.

20. The paint composition of claim 19, wherein the polymer base paint material comprises at least one material selected from the group consisting of a polyurethane, polyester, polypropylene, polybutylene, poly(L-lactic acid), polycellulosic, polyhydroxy alkanate, lignose cellulose, polyethylene oxide, epoxy, epoxy resin, alkyd resin, polyether, and mixtures of at least two of the foregoing.

* * * * *